(12) United States Patent
Engert et al.

(10) Patent No.: US 11,440,872 B2
(45) Date of Patent: Sep. 13, 2022

(54) CARBONIC ACID ADDUCTS

(71) Applicant: INFLAMED PHARMA GMBH, Jena (DE)

(72) Inventors: Beatrice Engert, Jena (DE); Susanne Vogelsang, Jena (DE)

(73) Assignee: INFLAMED PHARMA GMBH, Jena (DE)

( * ) Notice: Subject to any disclaimer, the term of this patent is extended or adjusted under 35 U.S.C. 154(b) by 133 days.

(21) Appl. No.: 16/644,909

(22) PCT Filed: Sep. 7, 2018

(86) PCT No.: PCT/EP2018/074089
§ 371 (c)(1),
(2) Date: Mar. 5, 2020

(87) PCT Pub. No.: WO2019/048590
PCT Pub. Date: Mar. 14, 2019

(65) Prior Publication Data
US 2020/0216384 A1    Jul. 9, 2020

(30) Foreign Application Priority Data
Sep. 7, 2017  (DE) ..................... 10 2017 120 564.0

(51) Int. Cl.
| C07C 233/07 | (2006.01) |
| A61K 47/02 | (2006.01) |
| C07C 229/60 | (2006.01) |
| C04B 24/04 | (2006.01) |
| C07C 227/14 | (2006.01) |

(52) U.S. Cl.
CPC ............ *C07C 233/07* (2013.01); *A61K 47/02* (2013.01); *C04B 24/04* (2013.01); *C07C 227/14* (2013.01); *C07C 229/60* (2013.01)

(58) Field of Classification Search
CPC .. A61K 2300/00; A61K 31/245; A61K 33/00; A61K 47/02; A61K 47/06; A61K 9/0019; A61K 9/06; A61K 9/2059; A61K 9/4866; A61P 11/16; A61P 25/28; A61P 29/00; A61P 35/00; C07C 211/63; C07C 229/60; C07C 233/07; C07C 237/04; C07C 227/14

See application file for complete search history.

(56) References Cited

U.S. PATENT DOCUMENTS
2008/0317729 A1    12/2008    Kasch et al.

FOREIGN PATENT DOCUMENTS

| CN | 102973494 A | | 3/2013 |
| DE | 102013015035 | * | 2/2015 |
| DE | 102013015035 A1 | * | 4/2015 |
| DE | 102013015035 A1 | | 4/2015 |
| GB | 349640 A | | 6/1931 |
| WO | 2018122626 A1 | | 7/2018 |

* cited by examiner

*Primary Examiner* — Jean P Cornet
(74) *Attorney, Agent, or Firm* — Kagan Binder, PLLC

(57) ABSTRACT

The present invention relates to a carbonic acid adduct (CAA) comprising carbonic acid, at least one amine, and optionally at least one salt, said adduct being producible by a method comprising the following steps: a) providing a solution (A) comprising dissolved $CO_2$; optionally b) dissolving a base (BA) not corresponding to the amine (AM) in the solution (A) so as to obtain the solution (A1); c) dissolving the at least one amine (AM) in the solution (A) or (A1) so as to obtain the solution (B); d) freezing the solution obtained after completion of step c); and e) storing the solution frozen in step d) at −100 to 0° C. for no longer than 4 days. The content of $CO_2$ in the solution that is subjected to step c) is at least 6 g/l. The invention also relates to a method for producing the carbonic acid adduct (CAA), a pharmaceutical preparation (PP) comprising the carbonic acid adduct (CAA), and methods for the production thereof and use of the carbonic acid adduct (CAA) or the pharmaceutical preparation (PP) in therapy for a range of indications.

9 Claims, 12 Drawing Sheets

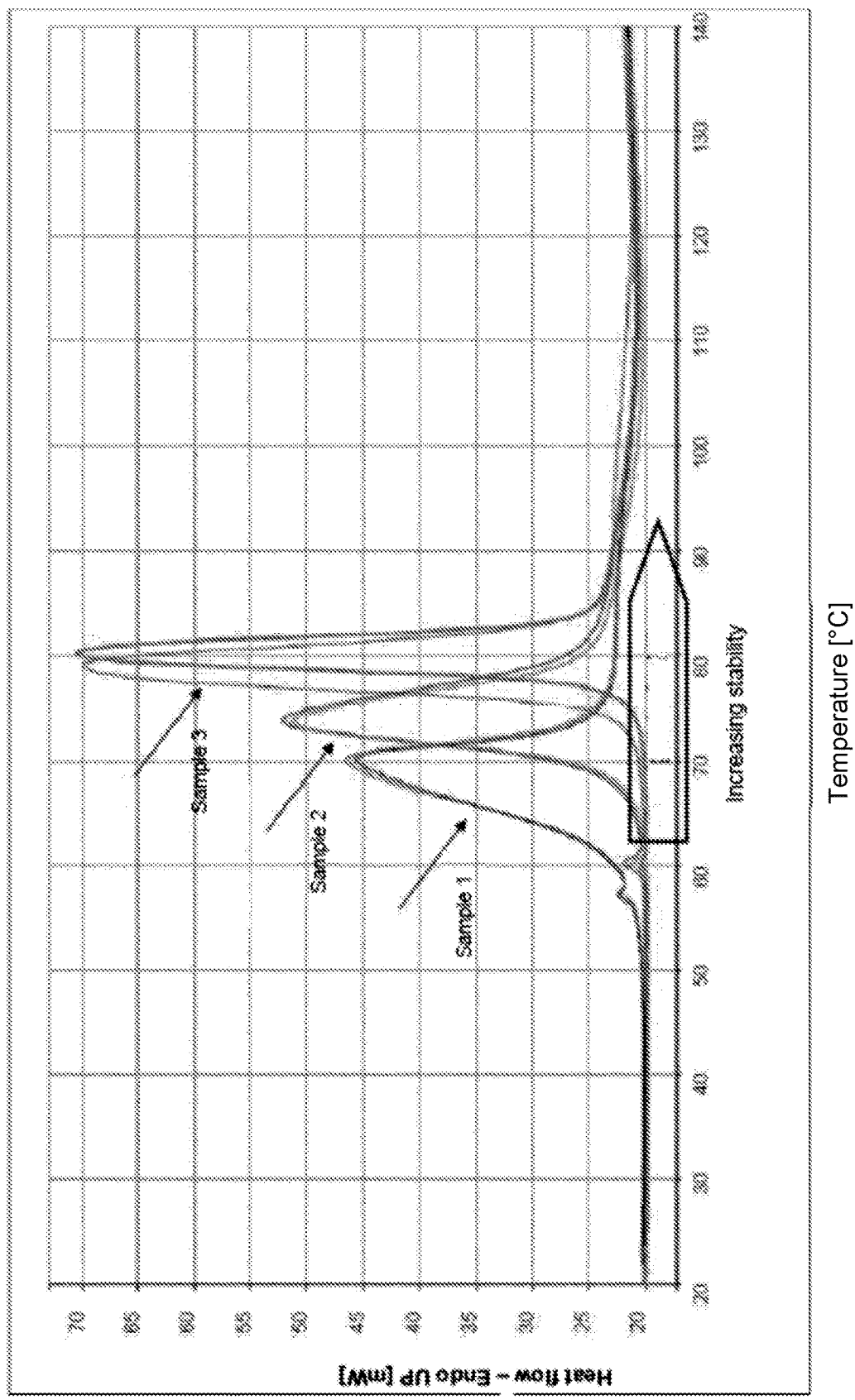
Fig. 1: comparative DSC tests of examples 2.8 (sample 1), 2.7 (sample 2) and 2.6 (sample 3).

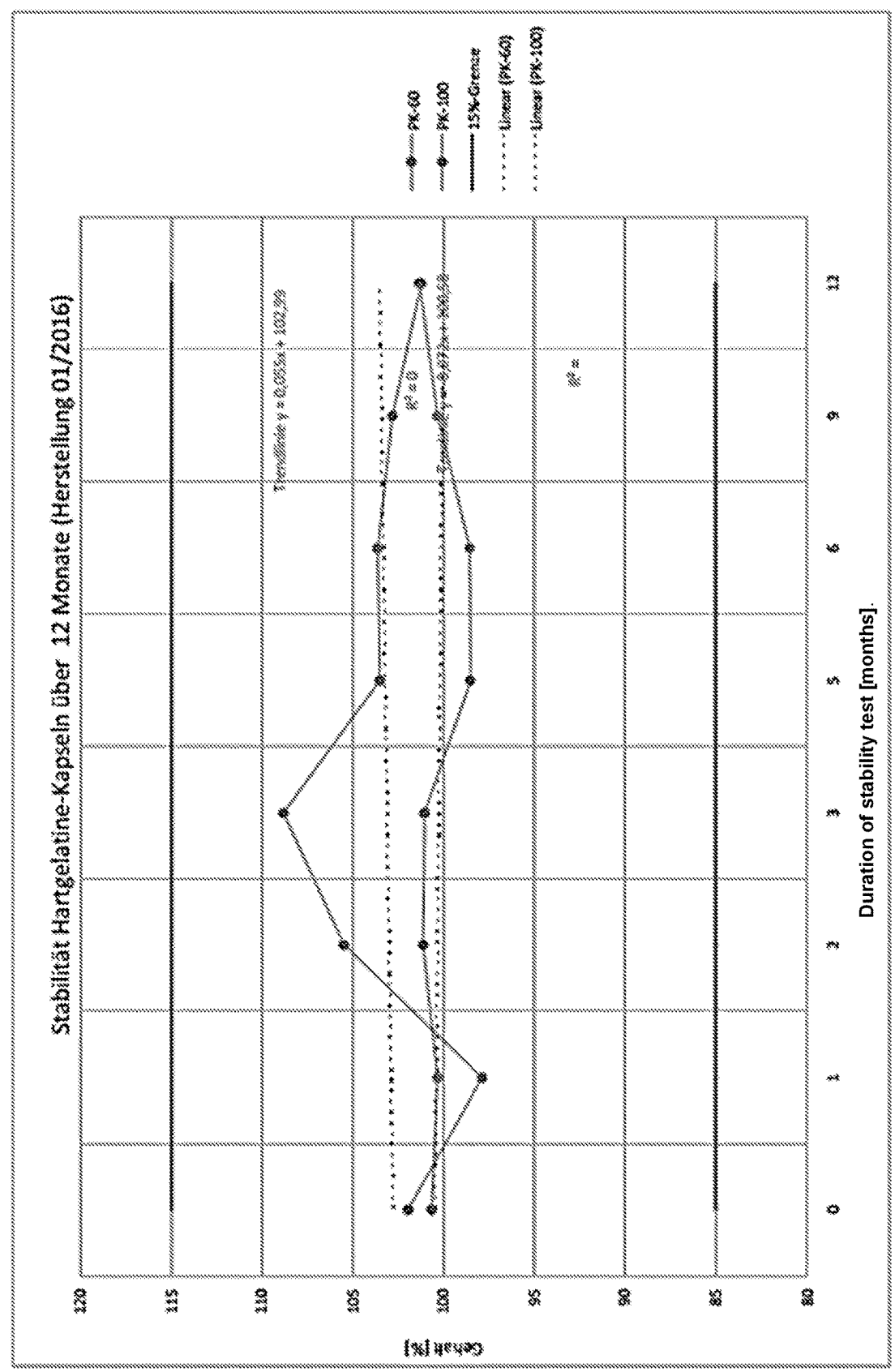
Fig. 2: stability test on hard gelatin capsules.

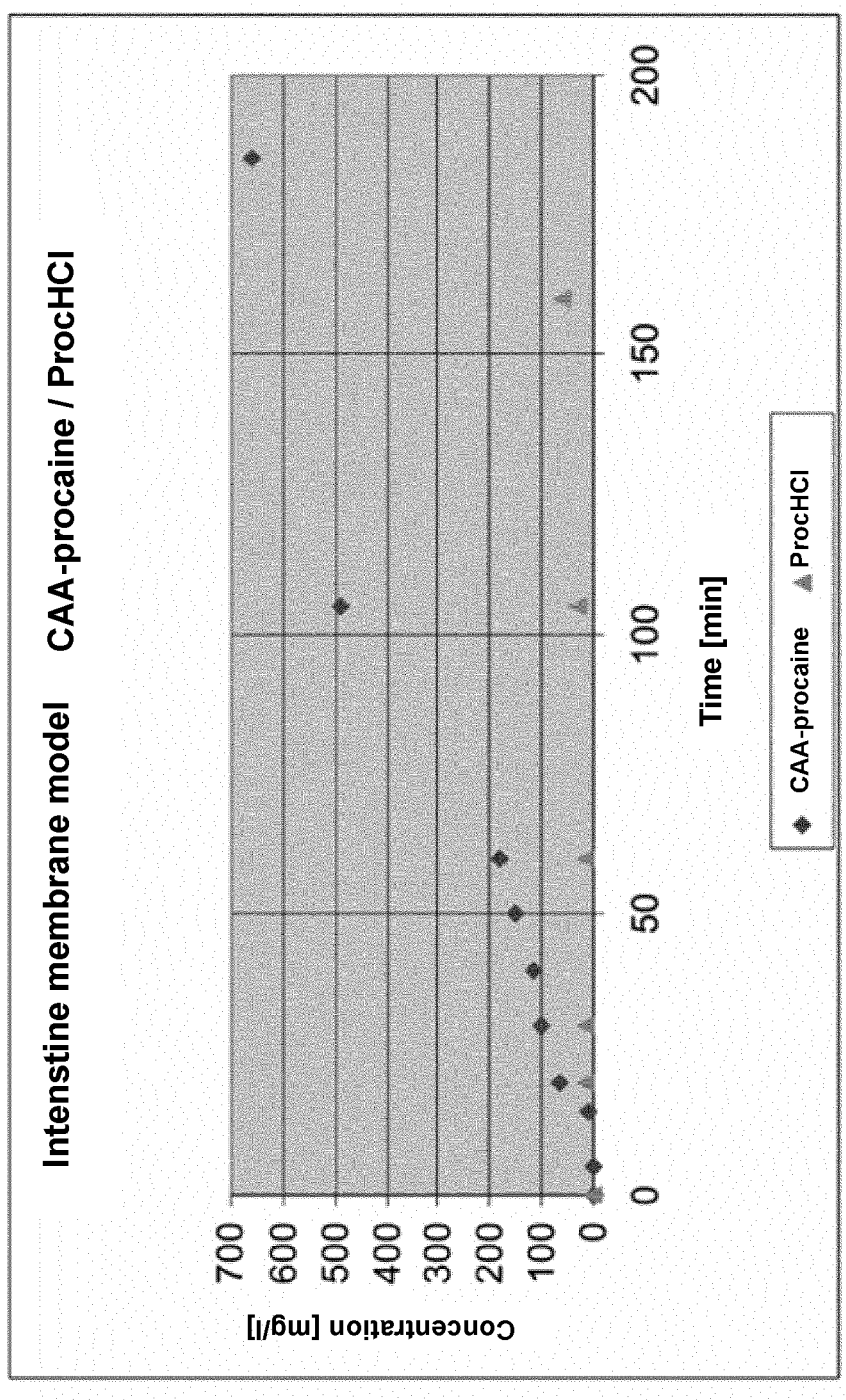
Fig. 3: diffusibility of the carbonic acid adduct (CAA), comprisng procaine as the amine (AM) (CAA-procaine), compared with procaine hydrochloride (ProcHCl)

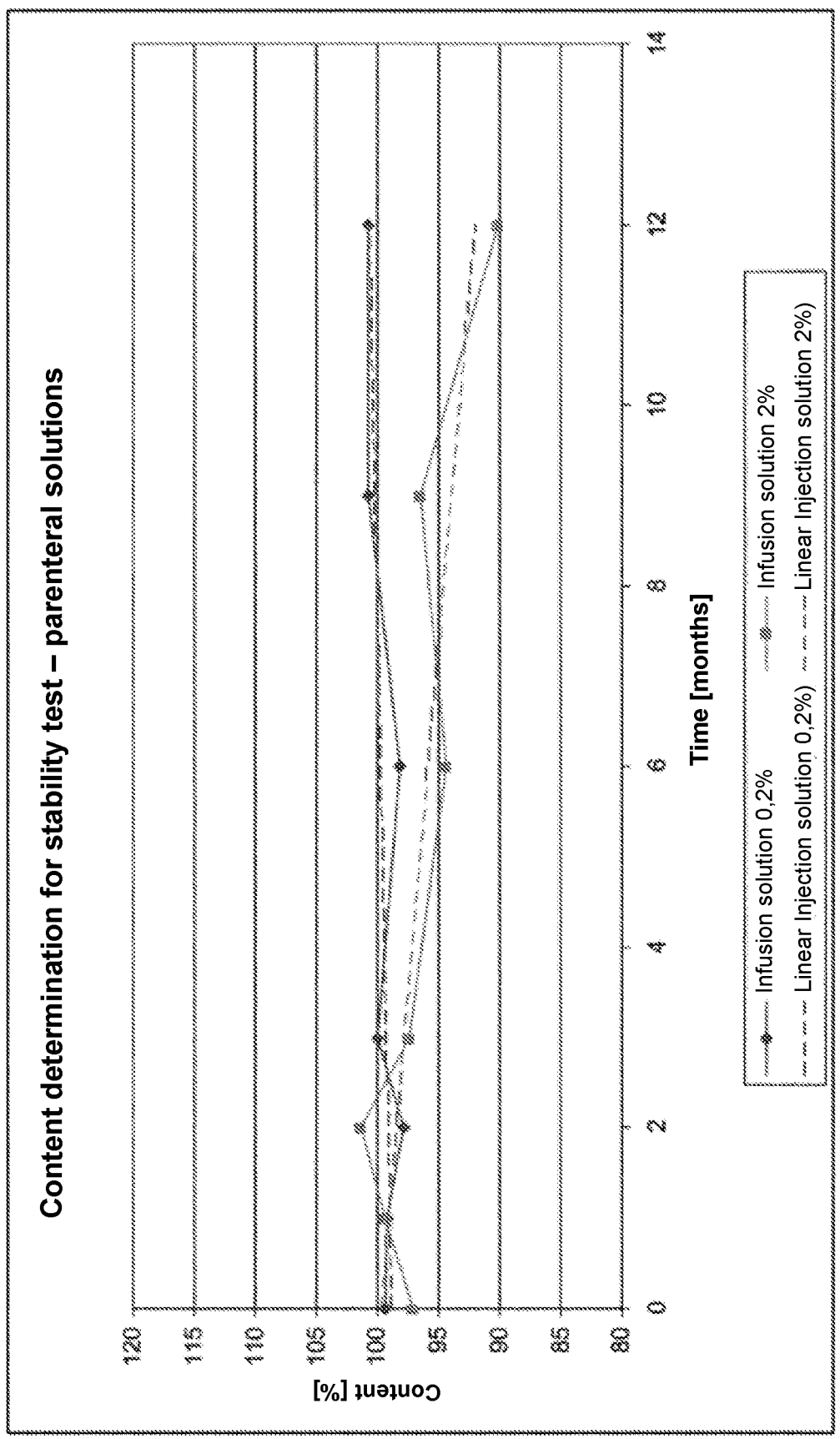
Fig. 4: comparison of the stability of a 0.2% infusion solution and the stability of a 2% injection solution.

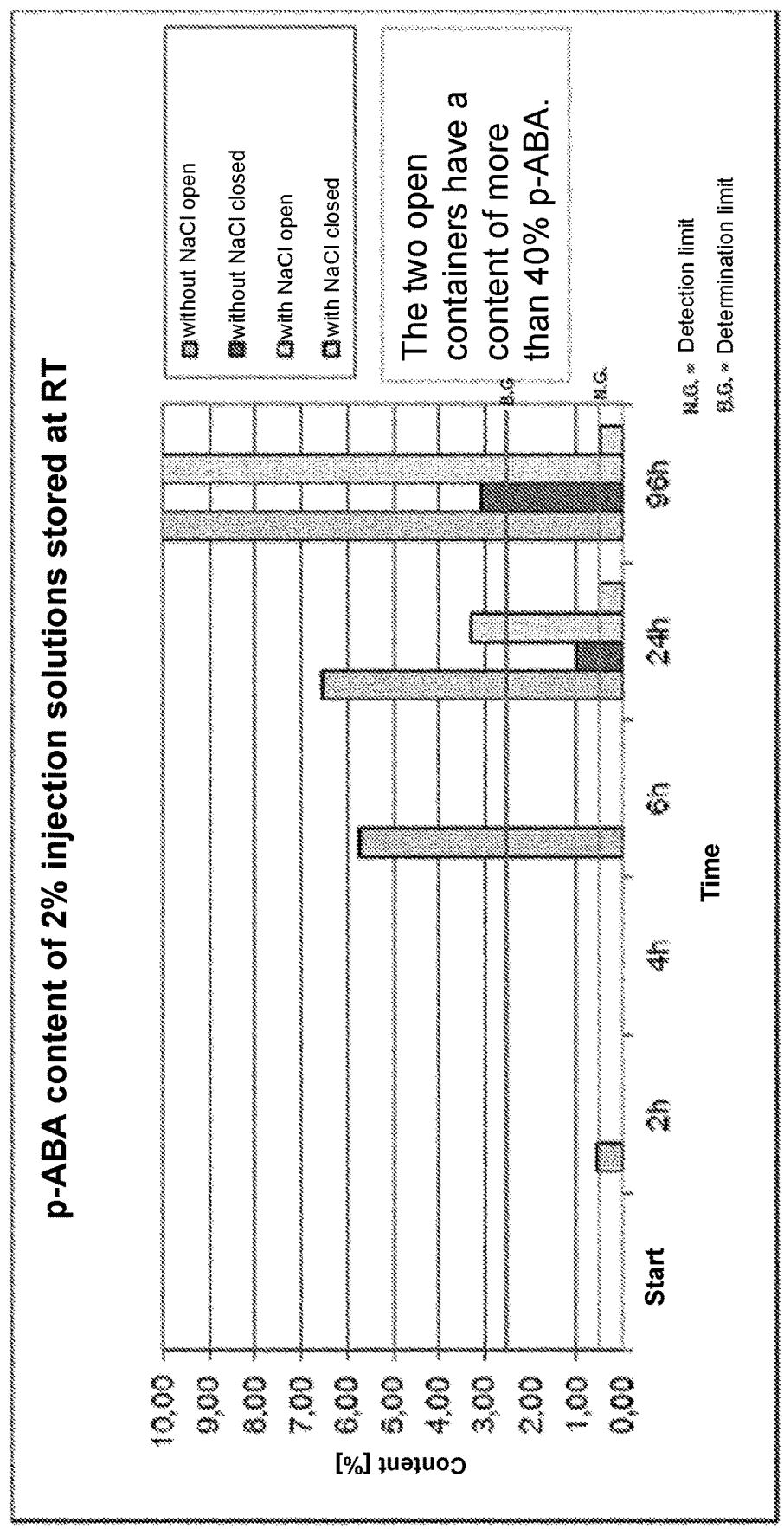
Fig. 5: influence of $CO_2$ and sodium chloride on the stability of a 2% injection solution

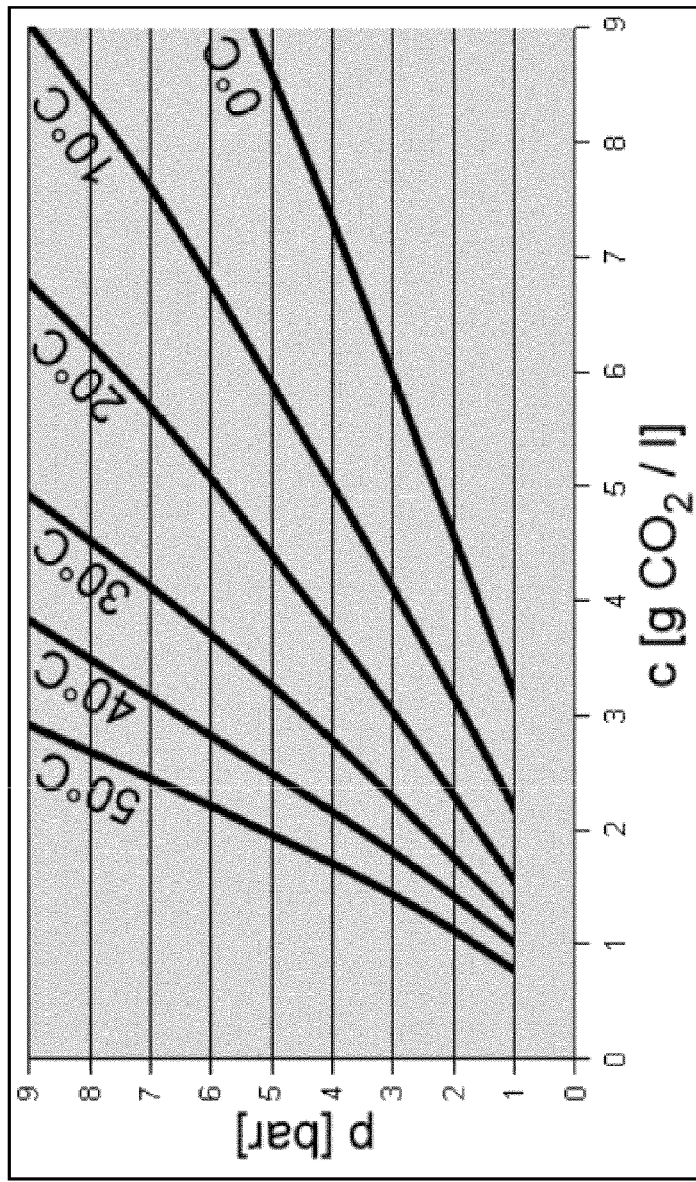
Fig. 6: water solubility of $CO_2$ depending on the pressure, at different temperatures
Source: https://de.wikipedia.org/wiki/Datei:Co2pctrp.png

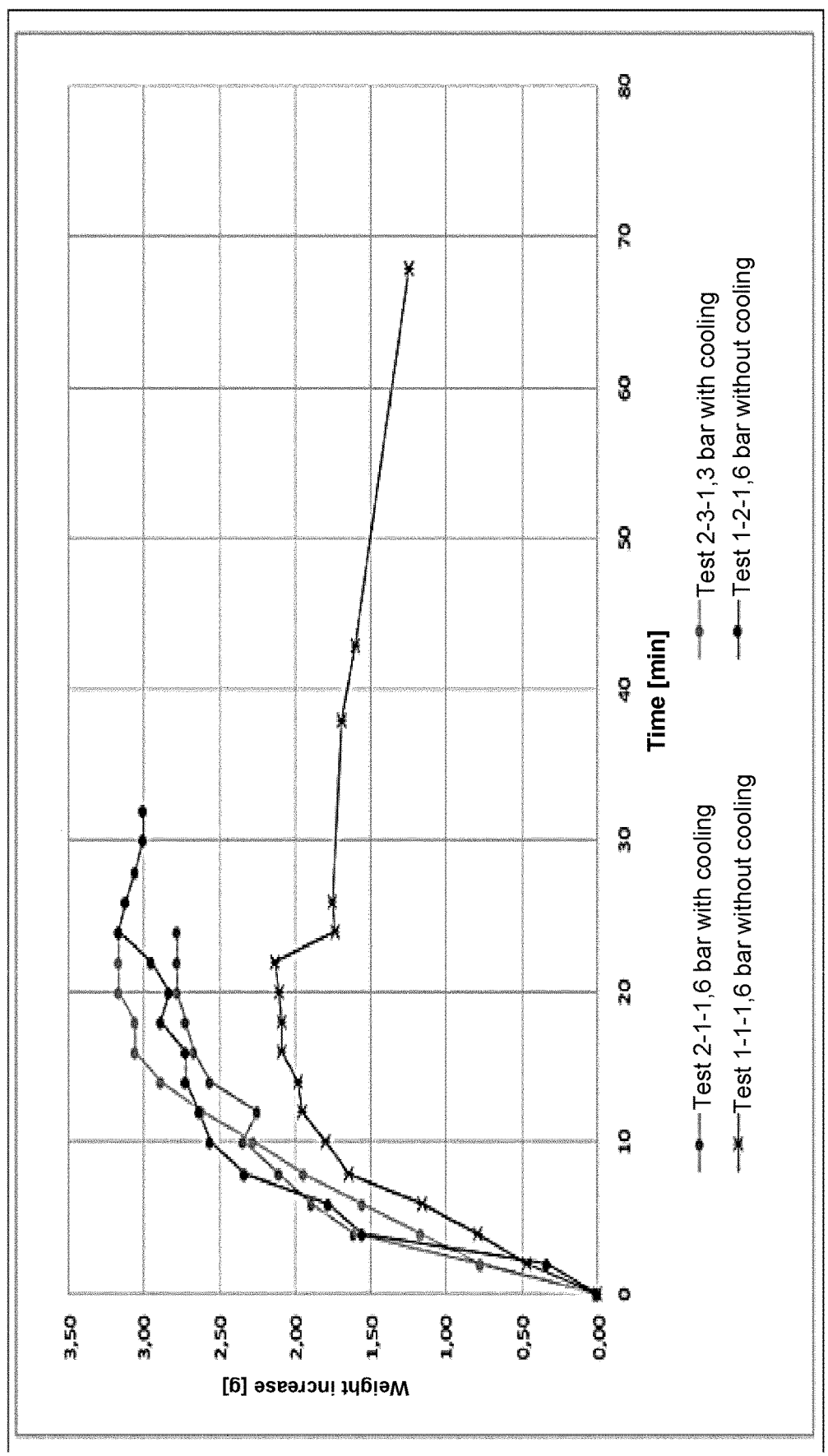
Fig. 7: CO$_2$-uptake of water depending on time

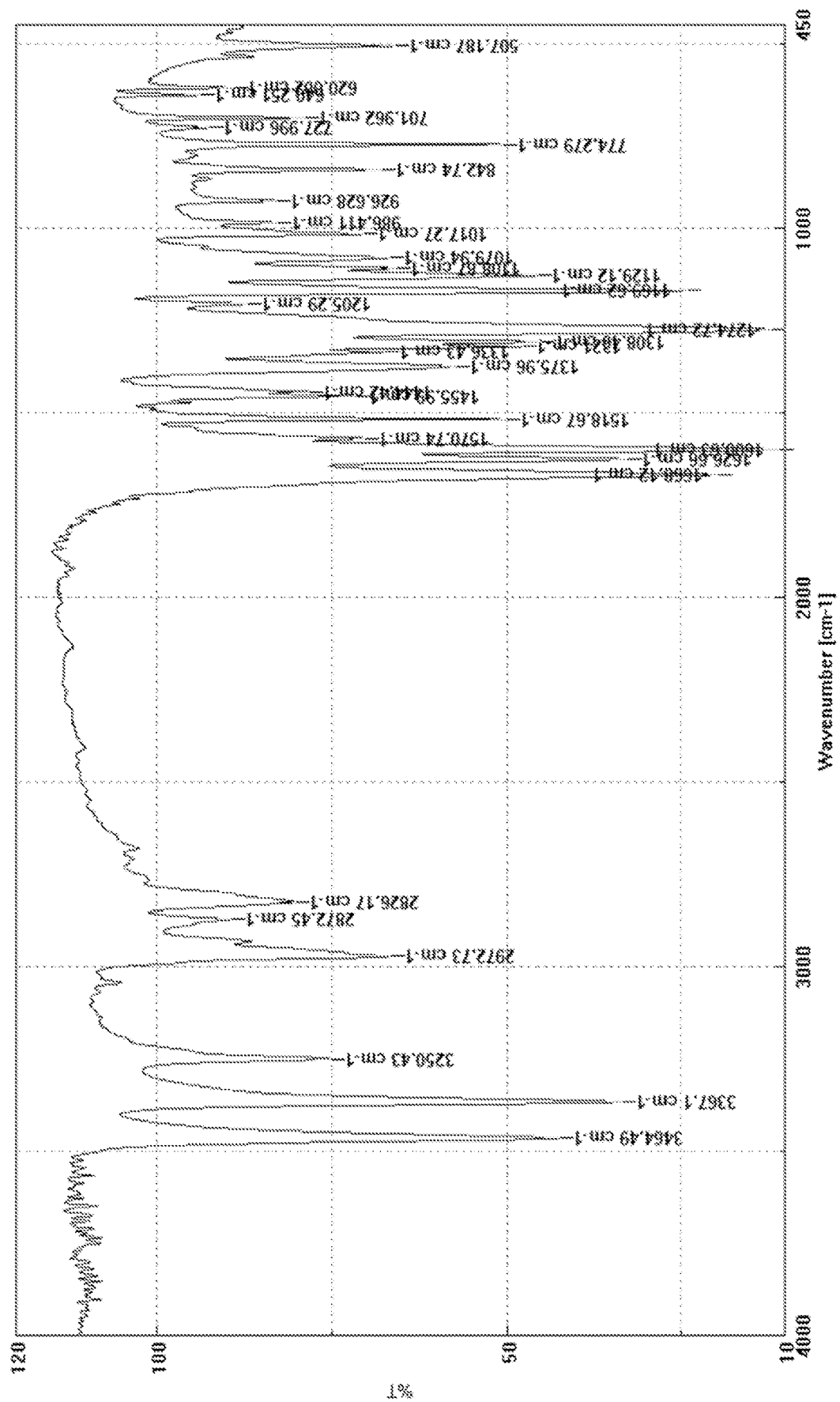
Fig. 8: infrared spectrum of procaine

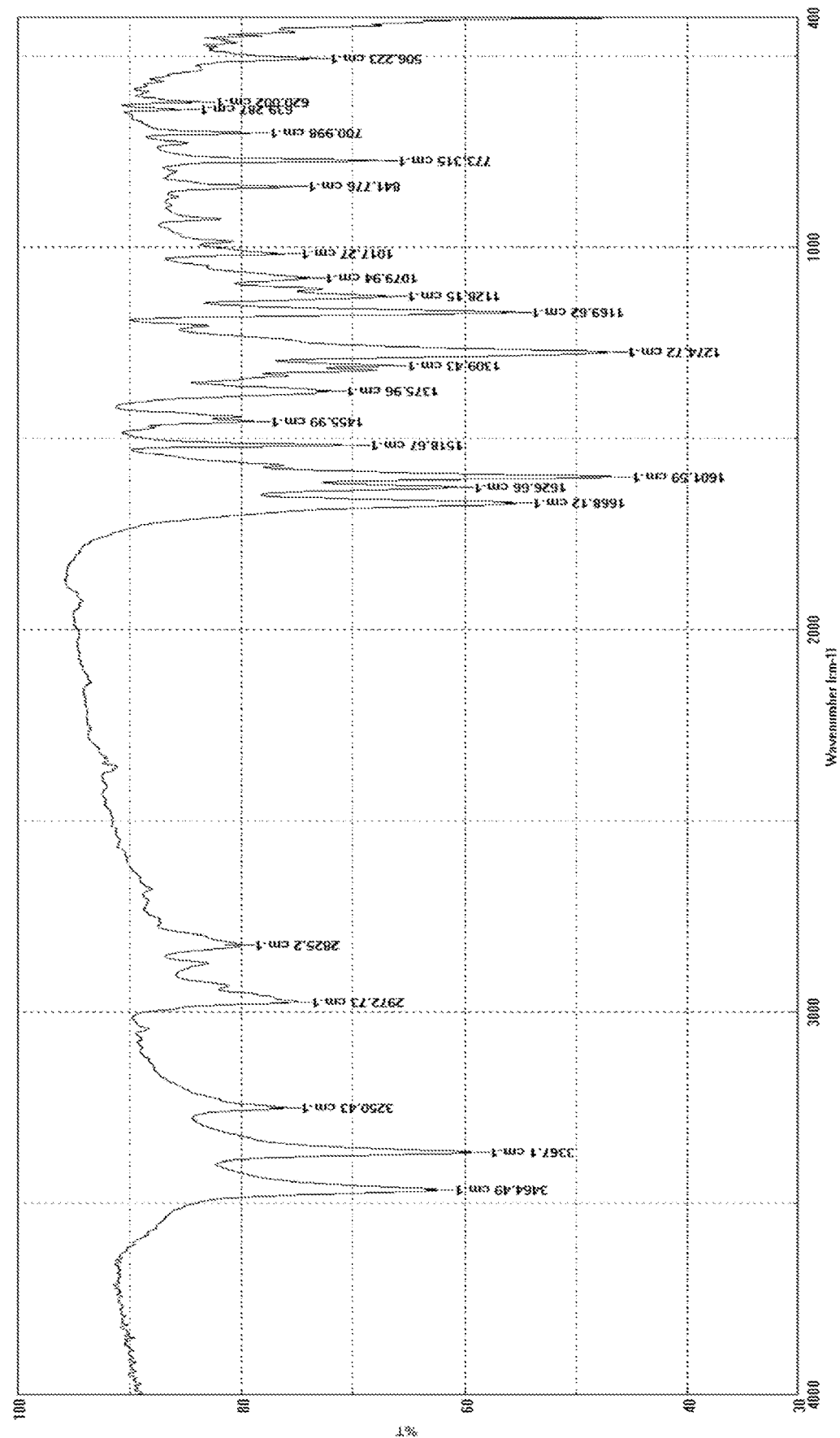
Fig. 9: infrared spectrum for the attempted preparation of carbonic acid adduct (CAA) from ProcHCl and $Na_2CO_3$, without addition of $CO_2$

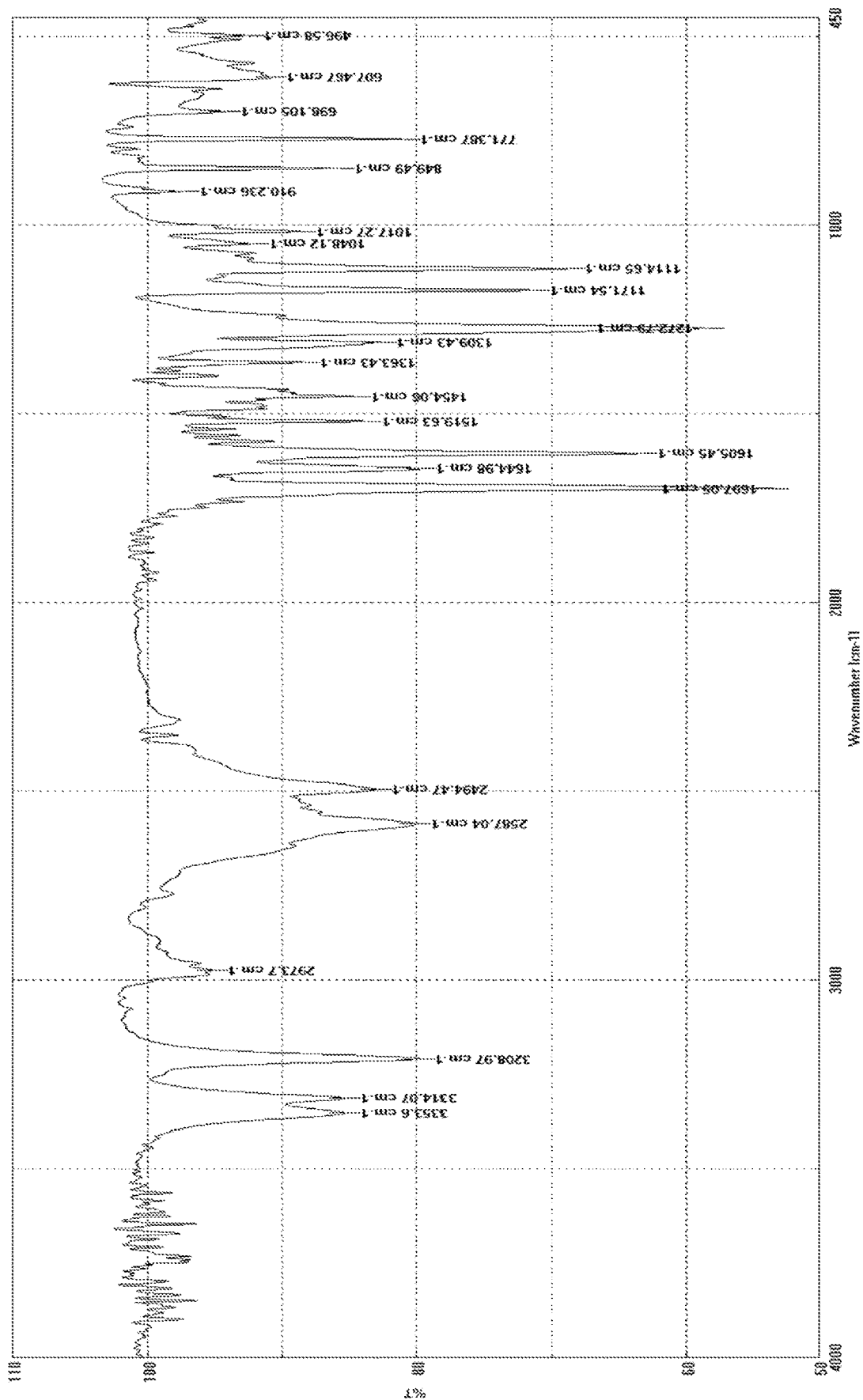
Fig. 10: infrared spectrum of procaine hydrochloride (ProcHCl)

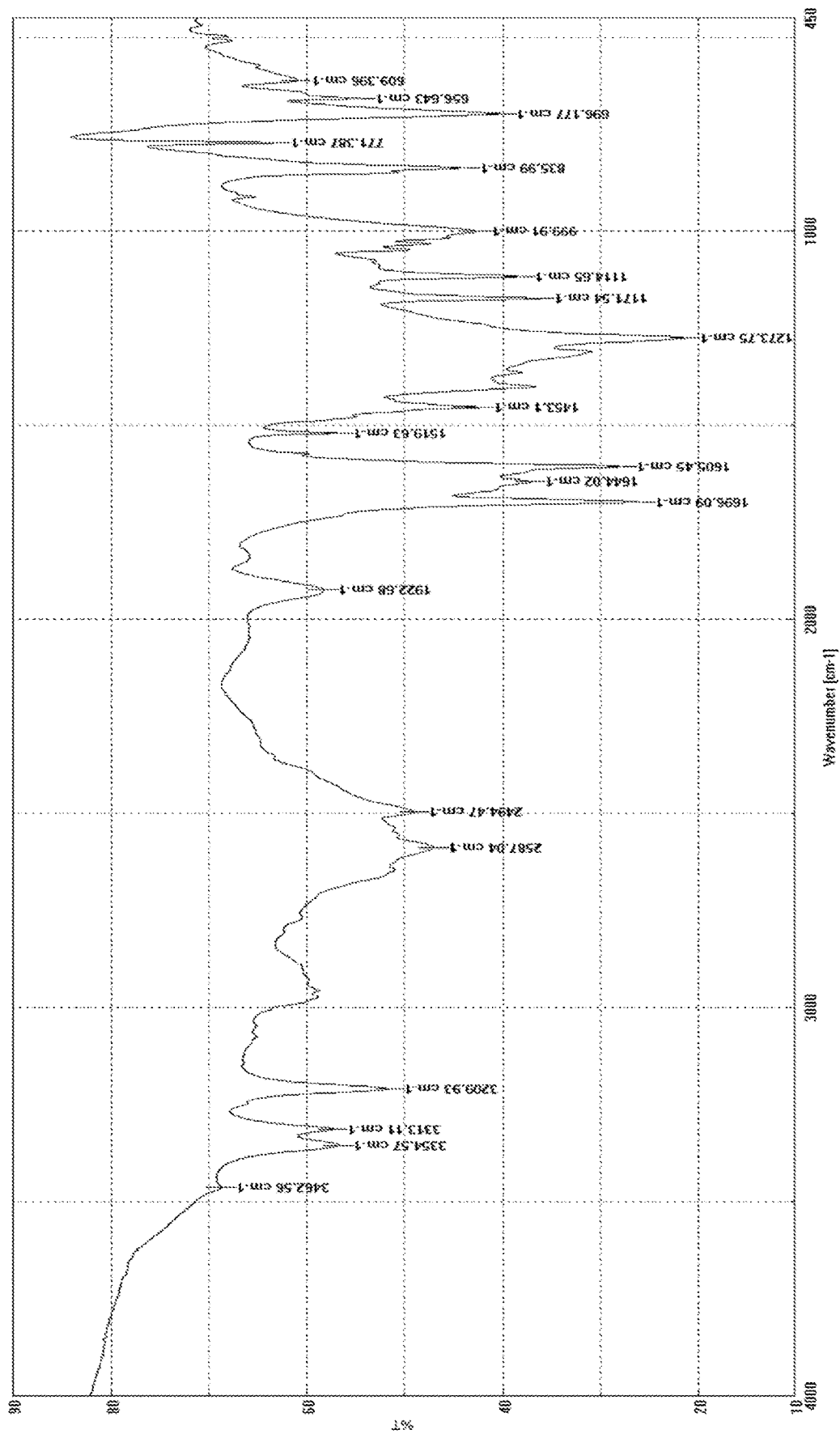
Fig. 11: mixture of carbonic acid adduct (CAA), together with procaine as the amine (AM) and NaHCO₃, in a molar ratio of 1:10

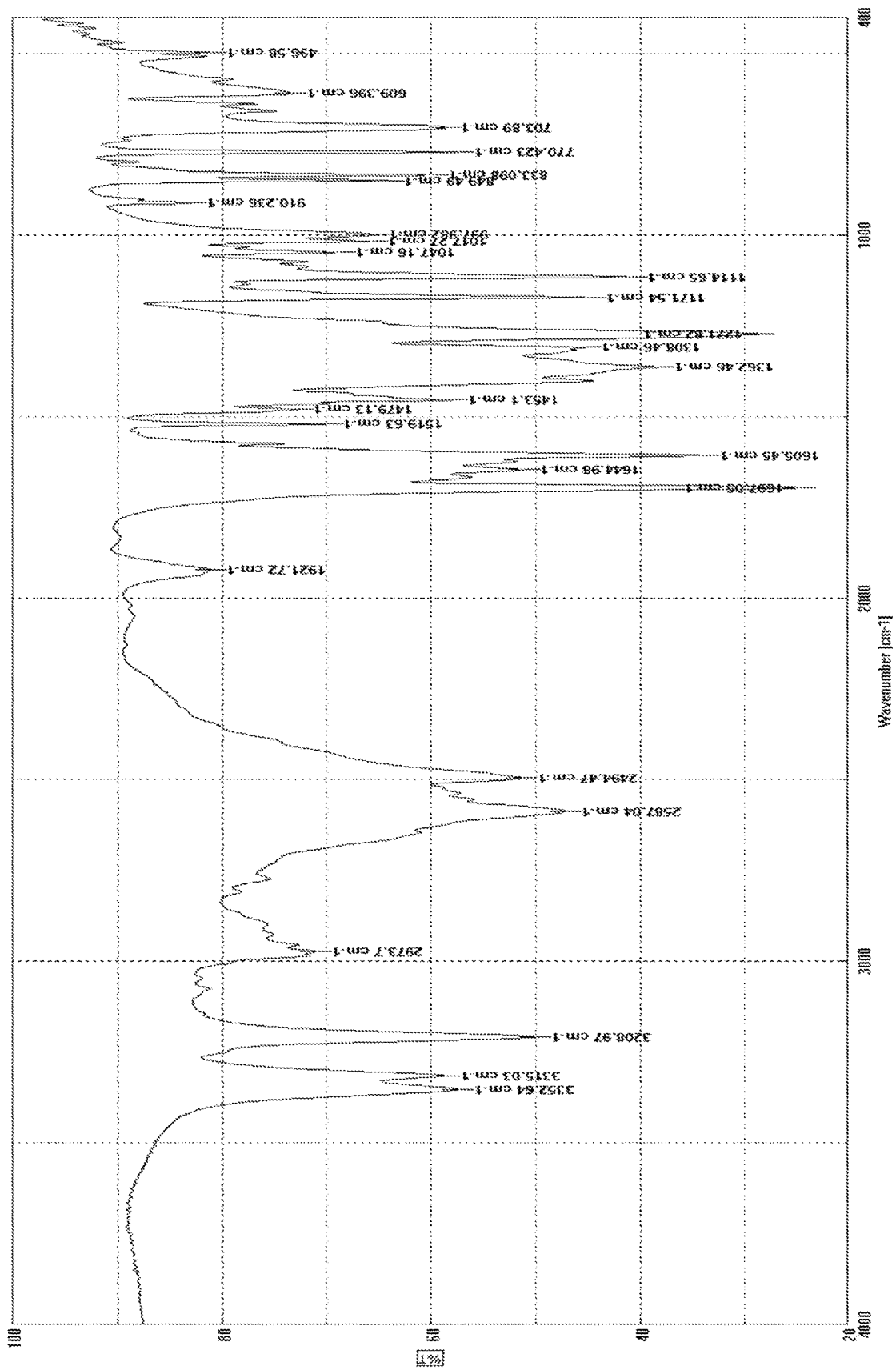
Fig. 12: infrared spectrum of the carbonic acid adduct (CAA) prepared according to embodiment 1

CARBONIC ACID ADDUCTS

CROSS REFERENCE TO RELATED APPLICATIONS

This application claims priority to International Application No. PCT/EP2018/074089, filed on Sep. 7, 2018, which claims the benefit of German Application No. 10 2017 120 564.0, filed Sep. 7, 2017, the content of which is incorporated by reference in its entirety.

TECHNICAL FIELD

The subject matter of the present invention relates to a carbonic acid adduct (CAA) that comprises carbonic acid, at least one amine, and optionally at least one salt, and that can be prepared according to a method comprising the steps of a) providing a solution (A) that comprises dissolved $CO_2$ optionally b) dissolving a base (BA), which does not correspond to the amine (AM), into the solution (A), thereby obtaining the solution (A1), c) dissolving the at least one amine (AM) in the solution (A) or (A1), thereby obtaining the solution (B), d) freezing the solution (B) obtained after completion of step c), and e) storing the solution frozen in step d) at −100 to 0° C. for no more than 4 days. The content of $CO_2$ in the solution that undergoes step c) being at least 6 g/l. The invention further relates to a method for preparing the carbonic acid adduct (CAA), a pharmaceutical preparation (PP) comprising the carbonic acid adduct (CAA), as well as methods for the preparation thereof and the use of the carbonic acid adduct (CAA) or the pharmaceutical preparation (PP) in treatment of a range of indications.

TECHNICAL BACKGROUND

As disclosed in WO2006/007835 A2, carbonic acid adducts of amines are of interest in particular for pharmaceutical/medical applications. In particular for the carbonic acid adduct of procaine, it is known from this disclosure that the transport of the active ingredient improves the bioavailability and the tolerability, inter alia in the case of acidosis. Likewise, an absence of hemolysis, in comparison with procaine, is observed. The cause of this is the presence of an acid-base pair consisting of the amine and carbonic acid, which has a high buffer capacity and is easily soluble. It is also explained that it is important for the stability of the procaine hydrogen carbonate to keep low the concentration of basic substances, such as procaine and carbonate, for example in the infusion solutions thereof. The basicity of the carbonate promotes saponification of the procaine. Furthermore, even small amounts of carbonate catalyze the breakdown of the procaine hydrogen carbonate into procaine and diprocainium carbonate. Incorporation into mineral salts such as sodium chloride and/or dextrane, starch or cellulose, to form clathrates or clusters, is cited as one option for stabilizing the procaine hydrogen carbonate or lidocaine hydrogen carbonate. Furthermore, the addition of $CO_2$ is required, as a result of which the pH is lowered and the fraction of the procaine hydrogen carbonate is brought to almost 100%. Using the procaine hydrogen carbonate as a salt cluster in the form of a powder, as capsules or tablets increases the tolerability yet further. Coating of the tablets owing to possible decomposition in the gastrointestinal passage is not essentially required, since a protective layer is formed during the pressing process, which layer is preferably dissolved in the intestine. Inter alia the possibility of nasal application thereof, and the systematic or local applicability thereof as anti-inflammatory agents, as a lower side-effect replacement for corticosteroids, are described as further advantages of the procaine hydrogen carbonate salt cluster.

The aim of application DE 10 2013 015 035 A1, which refers directly to WO2006/007835 A2, is that of improving some disadvantages of the above-described procaine carbonic acid mineral salt cluster by developing suitable formulations, such that said formulations are made suitable for pharmaceuticals, and thus meet higher requirements with respect to stability, effect and acceptance. For this purpose, a method for preparing carbonic acid mineral salt clusters of the procaine is described, as well as the use thereof in formulations for injection solutions, inhalation solutions, ointments and tablets. In a manner analogous to WO2006/007835 A2, the document discloses that, when preparing the procaine carbonic acid mineral salt cluster, both salt and $CO_2$ are present in the reaction solution.

However, carbonic acid adducts, comprising carbonic acid, at least one amine, and optionally at least one salt, which adducts are stable for a particularly long time and in particular have a high degree of storage stability, have hitherto not been described in the prior art. The influence of individual parameters on the storage stability is not discussed either. Carbonic acid adducts of this kind would, however, be desirable for commercial use, since the starting decomposition of the adducts into the starting amines thereof render said adducts unusable, in many cases, for pharmaceutical medical usage. Without a sufficient degree of storage stability, the corresponding compounds have to be prepared relatively at the last minute, which is made even more difficult if the carbonic acid adducts have to be prepared according to GMP conditions in order to achieve market authorization for medical-pharmaceutical purposes. In addition, more sensitive compounds have to be categorized in a different stability category (ICH (International Council for Harmonization of Technical Requirements for Pharmaceuticals for Human Use)—Table), which then places higher requirements on the storage and transport conditions, and is thus also more complex and costly from a GMP (Good Manufacturing Practice) perspective too.

According thereto, the aim of the present invention is that of providing a further carbonic acid adduct that corresponds to the higher requirements, as well as developing corresponding pharmaceutical preparations which comprise said carbonic acid adduct.

SUMMARY OF THE INVENTION

The invention relates to a carbonic acid adduct (CAA) comprising carbonic acid, at least one amine (AM), and optionally at least one salt (S)
which can be prepared according to a method comprising the steps of
a) providing a solution (A) which comprises at least one solvent, and $CO_2$ dissolved in the at least one solvent,
b) optionally dissolving a base (BA), which does not correspond to the amine (AM), in the solution (A), thereby obtaining the solution (A1),
c) dissolving the at least one amine (AM) in the solution (A) or (A1), thereby obtaining the solution (B),
d) freezing the solution obtained after completion of step c),
e) storing the solution frozen in step d) at −100 to 0° C. for no more than 4 days,
the content of $CO_2$ in the solution that undergoes step c) being at least 6 g/l, preferably at least 10 g/l, more preferably at least 12 g/l, even more preferably at least 14 g/l, and very particularly preferably at least 15 g/l, and it also being possible for the amine (AM) to be used in the form of a salt.

A further aspect of the invention sets out a method for preparing the carbonic acid adduct (CAA), according to the steps described above.

The invention furthermore relates to a carbonic acid adduct (CAA) that comprises at least one amine (AM), carbonic acid, and optionally a salt (S), and can be prepared according to the above-mentioned method,
i) the carbonic acid adduct (CAA) comprising procaine, carbonic acid and a salt (S), and the decomposition point being 65 to 95° C., preferably 70 to 90° C., more preferably 85 to 90° C. or
ii) comprising lidocaine, carbonic acid and a salt (S), and the decomposition point being 20 to 45° C., preferably 25 to 45° C., more preferably 30 to 45° C., and/or
iii) the carbonic acid adduct (CAA) remaining stable, during storage at a temperature of 2 to 10° C., for at least 12 months, preferably for at least 13 months, more preferably for at least 20 months, even more preferably for at least 23 months, particularly preferably for at least 27 months.

Furthermore, the invention also covers a pharmaceutical preparation (PP) comprising the carbonic acid adduct (CAA) according to one of the definitions above,
a) and optionally, during preparation of the pharmaceutical preparation (PP), the temperature is less than 60° C., preferably less than 50° C., more preferably 0 to 50° C., and/or
b) when using dispersers and/or ointment preparation means, a rotational speed of <2000 rpm is used, as well as methods and kits for the preparation thereof.

Moreover, the invention relates to the carbonic acid adduct (CAA) or the pharmaceutical preparation for use in a method for anesthesia, for analgesia, for concomitant treatment of cancer, for anti-inflammatory purposes, for promotion of wound healing, in particular in the case of burns, open wounds and scars, for treatment of neurogenic inflammation such as multiple sclerosis, MMN (multifocal motor neuropathy), for treatment of sinusitis, for treatment of asthma, for treatment of rheumatoid arthritis, for treatment of Alzheimer's, for treatment of dementia, for promotion of convalescence and for promotion of anti-aging, for treatment of burn-out syndromes, for treatment of osteoarthritis, for treatment of polyarthritis, for treatment of pain syndrome and general pain, for pre- and post-operative treatment (also in the case of broken bones), for preventative and rehabilitation medicine, for treatment of zoster neuralgia, for treatment of diseases of the abdominal organs, such as the liver, gall bladder, pancreas, intestine, for treatment of gastrointestinal diseases (ulcerative colitis, Crohn's disease), for treatment of Bekhterev's disease, for treatment of chronic pain of the musculoskeletal system, for treatment of diabetes (improvement of the blood sugar levels), for reducing edemata, and as comedication for opioids or other analgesics.

The carbonic acid adduct (CAA) according to the invention is characterized by a high degree of storage stability, and high decomposition temperatures. The carbonic acid adducts (CAA) also have a significantly higher dissolution rate, in particular in water, than the underlying amines or the salts thereof.

Furthermore, the carbonic acid adduct (CAA) according to the invention exhibits ambiphilic properties which makes it particularly suitable, when used as an active ingredient for forms of application, preferably also in the form of a pharmaceutical preparation (PP), that require an increased level of diffusibility. Furthermore, after entering the organism, the ambiphilic nature of the carbonic acid adduct also makes it easier to transport said adduct to the site of actin, and thus makes it possible to save on active ingredient.

When the carbonic acid adduct (CAA is applied as an active ingredient, the buffer effect which is achieved by the presence of the at least one amine (AM) and carbonic acid leads to a reduced toxicity and improved tolerability than is the case when the salt of the amine is administered alone.

BRIEF DESCRIPTION OF THE FIGURES

FIG. 1: shows comparative DSC tests of examples 2.8 (sample 1), 2.7 (sample 2) and 2.6 (sample 3).

FIG. 2: shows a stability test on hard gelatin capsules. As described in detail in example 4.1, hard gelatin capsules having 60 and 100 mg active ingredient, according to table 3, underwent a stability test over a time period of 12 months.

FIG. 3: shows the diffusibility of the carbonic acid adduct (CAA), comprising procaine as the amine (AM) (CAA-procaine), compared with procaine hydrochloride (ProcHCl). As described in example 4.3, in FIG. 3 the concentration of the substance tested in each case, in a solution and after passing through a pig intestine, is plotted over time.

FIG. 4: shows a comparison of the stability of a 0.2% infusion solution and the stability of a 2% injection solution. As described in detail in example 4.4.1, the stability of two parenteral solutions over a time period of 12 months was compared.

FIG. 5: the influence of $CO_2$ and sodium chloride on the stability of a 2% injection solution was compared, at room temperature and over a time period of 96 h. Further details are described in example 4.4.2.

FIG. 6: shows the water solubility of $CO_2$ depending on the pressure, at different temperatures.

FIG. 7: shows the $CO_2$-uptake of water depending on time; in the tests involving cooling the temperature was 8° C.

FIG. 8: shows the infrared spectrum of procaine. In this case, the band at 3464 $cm^{-1}$ is characteristic.

FIG. 9: shows an infrared spectrum for the attempted preparation of carbonic acid adduct (CAA) from ProcHCl and $Na_2CO_3$, without addition of $CO_2$. The characteristic band of procaine at is clearly identifiable 3464 $cm^{-1}$, while no carbonic acid adduct is formed.

FIG. 10: shows the infrared spectrum of procaine hydrochloride.

FIG. 11: shows the infrared spectrum of a solids mixture consisting of carbonic acid adduct (CAA), together with procaine as the amine (AM) and $NaHCO_3$, in a molar ratio of 1:10. The beginning of the procaine formation at the band of 1:10. The beginning of the procaine formation at the band 3462.56 $cm^{-1}$ can be seen.

FIG. 12: shows the infrared spectrum of the carbonic acid adduct (CAA) prepared according to embodiment 1. There is no procaine band in the range 3461-3467 $cm^{-1}$.

DETAILED DESCRIPTION OF THE INVENTION

The carbonic acid adduct (CAA) comprises carbonic acid, at least one amine (AM), and optionally at least one salt (S).

Within the context of this invention, an adduct is understood to be a molecule which is formed by combination of smaller molecules, based on the molecular weight thereof, as the adduct, by way of the formation of covalent or non-covalent bonds, preferably non-covalent bonds. As non-covalent bonds the adduct preferably also comprises ionic bonds between at least some of the particles that have combined to form the adduct.

Carbonic acid, $H_2CO_3$, can be present in the carbonic acid adduct (CAA) both in non-ionized form, in partially ionized form, or completely ionized. These different degrees of ionization of the carbonic acid can also be present side-by-side, in the carbonic acid adduct. The ionization of the carbonic acid can be achieved by transfer of one or both protons of the carbonic acid to another molecule, preferably of at least one proton to the amine (AM).

The at least one amine (AM) is understood to be a molecule which comprises at least one amino group, preferably one amino group. The amino group may be a primary, secondary or tertiary amino group.

The at least one amino group of the amine (AM) can be present in the carbonic acid adduct (CAA) both in neutral form and in protonated form. If the amine (AM) comprises more than one amino group, all the amino groups can be present in neutral form or all the amino groups can be present in protonated form, or some of the amino groups can be present in neutral form and some for the amino groups can be present in protonated form. Preferably at least one amino group is present in protonated form.

The carbonic acid adduct preferably comprises at least one amine (AM) according to one of the following formulae (I) and/or (II).

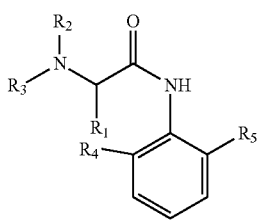

(I)

In which, in formula (I)

$R_1$ is H, $C_{1-10}$ alkyl, $C_{2-10}$ alkenyl, aryl or heteroaryl, preferably H or $C_{1-10}$ alkyl, more preferably H or $C_{1-4}$ alkyl;

$R_2$ is H, $C_{1-10}$ alkyl, $C_{2-10}$ alkenyl, aryl or heteroaryl, preferably H or $C_{1-10}$ alkyl, more preferably H or $C_{1-4}$ alkyl;

$R_3$ is H, $C_{1-10}$ alkyl, $C_{2-10}$ alkenyl, aryl or heteroaryl, preferably H or $C_{1-10}$ alkyl, more preferably H or $C_{1-4}$ alkyl;

it optionally being possible for $R_1$ and $R_3$ to be linked together and to form a saturated or unsaturated, preferably a saturated ring, together with the nitrogen atom to which $R_3$ is bound and the carbon atom to which $R_1$ is bound. The ring is preferably 4, 5 or 6-membered, more preferably 5 or 6-membered;

$R_4$ is H, halogen, $C_{1-10}$ alkyl, $C_{2-10}$ alkenyl, aryl, heteroaryl, preferably H or methyl;

$R_5$ is H, halogen, $C_{1-10}$ alkyl, $C_{2-10}$ alkenyl, aryl or heteroaryl, preferably H or methyl or halogen;

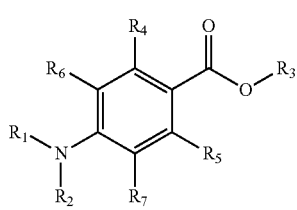

(II)

in which, in formula (II)

$R_1$ is H, $C_{1-10}$ alkyl, $C_{2-10}$ alkenyl, aryl or heteroaryl, preferably H or $C_{1-10}$ alkyl, more preferably H;

$R_2$ is H, $C_{1-10}$ alkyl, $C_{2-10}$ alkenyl, aryl or heteroaryl, preferably H or $C_{1-10}$ alkyl, more preferably H;

$R_3$ is H, $C_{1-10}$ alkyl, $C_{2-10}$ alkenyl, aryl, heteroaryl or —$(CH_2)_nNR_8R_9$, preferably —$(CH_2)_nNR_8R_9$;

n is 1 to 5, preferably 1 to 3, more preferably 1 to 2;

$R_8$ is $C_{1-10}$ alkyl, preferably $C_{1-2}$ alkyl;

$R_9$ is $C_{1-10}$ alkyl, preferably $C_{1-2}$ alkyl;

$R_4$ is H, halogen, $C_{1-10}$ alkyl, $C_{2-10}$ alkenyl, aryl, heteroaryl or —O—$C_{1-10}$ alkyl, preferably H, halogen, $C_{1-10}$ alkyl or —O—$C_{1-10}$ alkyl, more preferably H or halogen;

$R_5$ is H, halogen, $C_{1-10}$ alkyl, $C_{2-10}$ alkenyl, aryl, heteroaryl or alkyl, preferably H, halogen, $C_{1-10}$ alkyl or —O—$C_{1-10}$ alkyl, more preferably H or halogen;

$R_6$ is H, halogen, $C_{1-10}$ alkyl, $C_{2-10}$ alkenyl, aryl, heteroaryl or —O—$C_{1-10}$ alkyl, preferably H, halogen, $C_{1-10}$ alkyl or alkyl, more preferably H or alkyl;

$R_7$ is H, halogen, $C_{1-10}$ alkyl, $C_{2-10}$ alkenyl, aryl, heteroaryl or —O—$C_{1-10}$ alkyl, preferably H, halogen, $C_{1-10}$ alkyl or alkyl, more preferably H or —O—$C_{1-10}$ alkyl.

In the present invention, definitions such as $C_{1-10}$ alkyl, as defined for example for the group $R_1$ of formula (I) mean that this substituent (group) is a saturated alkyl group having a number of carbon atoms of from 1 to 10. The alkyl group can be linear, or branched, or optionally cyclic. Alkyl groups which comprise both a cyclic and a linear component are also covered by this definition. The same applies for other alkyl groups such as a $C_{1-2}$ alkyl group. Single or multiple substitution of the alkyl groups with functional groups such as amino, hydroxyl, halogen, aryl or heteroaryl is optionally also possible. Unless otherwise specified, alkyl groups preferably do not comprise any functional groups as substituents. Examples for alkyl groups are methyl, ethyl, n-propyl, n-butyl, n-pentyl, n-hexyl, n-heptyl, n-octyl, n-nonyl, isopropyl (also referred to as 2-propyl or 1-methylethyl), isobutyl, tert-butyl, sec-pentyl, neo-pentyl, 1,2-dimethylpropyl, isoamyl, isohexyl, isoheptyl.

In the present invention, definitions such as $C_{2-10}$ alkenyl, as defined for example for the group $R_1$ of formula (I), mean that this substituent (group) is an alkyl group having a number of carbon atoms of from 2 to 10 and comprising at least one unsaturated carbon-carbon bond. The alkenyl group can be linear, or branched, or optionally cyclic. Alkenyl groups which comprise both a cyclic and a linear component are also covered by this definition. The same applies for other alkenyl group such as a $C_{2-4}$ alkenyl group. Single or multiple substitution of alkenyl groups with functional groups such as amino, hydroxyl, halogen, aryl or heteroaryl is optionally also possible. Unless otherwise specified, alkenyl groups preferably do not comprise any functional groups as substituents. Examples for alkenyl groups are vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 3-heptenyl, 4-heptenyl, 1-octenyl, 3-octenyl, 5-octenyl, 1-nonenyl, 2-nonenyl.

In the present invention, definitions such as $C_{2-10}$ alkenyl, as defined for example for the group $R_1$ of formula (I), mean that this substituent (group) is an alkenyl group having a number of carbon atoms of from 2 to 10 and comprising at least one unsaturated carbon-carbon bond. The alkenyl group can be linear, or branched, or optionally cyclic. Alkenyl groups which comprise both a cyclic and a linear component are also covered by this definition. The same applies for other alkenyl group such as a $C_{2-4}$ alkenyl group.

Single or multiple substitution of alkenyl groups with functional groups such as amino, hydroxyl, halogen, aryl or heteroaryl is optionally also possible. Unless otherwise specified, alkenyl groups preferably do not comprise any functional groups as substituents. Examples for alkenyl groups are vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 3-heptenyl, 4-heptenyl, 1-octenyl, 3-octenyl, 5-octenyl, 1-nonenyl, 2-nonenyl.

In the present invention, the definition aryl means that this is an aromatic or heteroaromatic group. An aromatic group is an aromatic cyclic hydrocarbon which can consist of a ring or a ring system comprising a plurality of condensed rings. The aromatic group can for example be monocyclic, bicyclic or tricyclic. The monocyclic aromatic group preferably forms a 5- or 6-member ring. The bicyclic aromatic ring preferably forms a 9- or 10-member ring. The tricyclic aromatic ring preferably forms a 13- or 14-member ring. The aryl group preferably comprises 3 to 14, more preferably 4 to 6, carbon atoms. Single or multiple substitution of the aryl groups with functional groups such as alkyl, alkenyl, amino, hydroxyl, halogen, aryl or heteroaryl is optionally also possible. Examples for aromatic groups are phenyl and naphtyl.

In the present invention, the definition heteroaryl means that this is a heteroaromatic group. Heteroaromatic ring means that, in the case of an aromatic group as described above, the ring system of which is formed by carbon atoms, one or more of said carbon atoms is/are replaced by heteroatoms such as O, N or S. Examples for the heteroaromatic groups that, in the present invention, come under the definition aryl are furanyl, thienyl, oxazolyl, pyrazolyl, pyridyl and indolyl.

In the present invention, the definition halogen, as defined for example above for the group $R_4$ for formula (I), means that this is a chloro-, bromo-, iodo- or fluorosubstituent. This is preferably a chloro- or fluorosubstituent.

More preferably, the carbonic acid adduct (CAA) comprises at least one amine (AM) selected from the group consisting of 4-aminobenzoic acid-2-(N,N-diethylamino-)ethylester (procaine), 4-aminobenzoic acid ethyl ester (benzocaine), 2-(diethylamino)ethyl-4-amino-2-chlorobenzoate (chloroprocaine), 4-amino-3-butoxybenzoic acid-2-diethylaminoethylester (oxybuprocaine), (2-(dimethylamino)ethyl)-4-(butylamino)benzoate (tetracaine), N-[3-(4-phenoxymethylphenyl)propyl]morpholine (fomocaine), 2-diethylamino-N-(2,6-dimethylphenyl)acetamide (lidocaine), (RS)—N-(2,6-dimethylphenyl)-1-methylpiperidin-2-carboxamide (mepivacaine), (RS)—N-(2-methylphenyl)-2-(propylamino)-propanamide (prilocaine), (RS)-4-methyl-3-[2-(propylamino)-propanamido]thiophene-2-carboxylic acid methyl ester (articaine), (±)-1-Butyl-N-(2,6-dimethylphenyl)-2-piperidincarboxamide (bupivacaine), (S)-1-propyl-2',6'-dimethyl-2-piperidylcarboxyanilide (ropivacaine), 2-(ethylpropylamino)-2',6'-butyroxylidide (etidocaine) and 1-(4-butoxyphenyl)-3-piperidin-1-ylpropan-1-one (dyclonine).

Even more preferably, the carbonic acid adduct (CAA) comprises at least one amine selected from the group consisting of 4-aminobenzoic acid-2-(N,N-diethylamino-)ethylester (procaine), 2-diethylamino-N-(2,6-dimethylphenyl)acetamide (lidocaine), and (2-(dimethylamino)ethyl)-4-(butylamino)benzoate (tetracaine).

Particularly preferably, the carbonic acid adduct (CAA) comprises at least one amine (AM) selected from the group consisting of 4-aminobenzoic acid-2-(N,N-diethylamino-)ethylester (procaine), and 2-diethylamino-N-(2,6-dimethylphenyl)acetamide (lidocaine).

Very particularly preferably, the carbonic acid adduct (CAA) comprises 4-aminobenzoic acid-2-(N,N-diethylamino-)ethylester (procaine) as the amine (AM).

The carbonic acid adduct (AM) optionally comprises at least one salt (S). The carbonic acid adduct (AM) preferably comprises at least one salt (S). The carbonic acid adduct (AM) preferably comprises at least one salt (S) when the amine (AM) is procaine or lidocaine.

The salt (S) is preferably a salt that is composed of at one cation selected from $Na^+$, $K^+$, $Li^+$, $Mg^{2+}$, $Zn^{2+}$, $Fe^{2+}$, $Fe^{3+}$ and $Mn^{2+}$, and at least one anion selected from $Cl^-$, $Br^-$, $J^-$, $F^-$, $SO_4^{2-}$, $SO_3^{2-}$, $HSO_4^-$ $HSO_3^-$, —$HCO_3^-$, $CO_3^{2-}$, $PO_4^{3-}$, $HPO_4^{2-}$, $H_2PO_4^-$, $SiO_4^{4-}$, $AlO_2^-$, $SiO_3$ and/or $[AlO_2)_{12}(SiO_2)_2]^{2-}$. More preferably, the cation is selected from $Na^+$, and the anion is selected from $Cl^-$ or $Br^-$. The salt can be formed for example by means of an acid-base reaction of the base (BA), when carrying out step b), with the acid added to the amine (AM), if an acid additional salt of the amine (AM) is used. The salt (S) can also be directly added in one of steps a), b) and/or c). Direct addition of the salt (S) is preferred if the amine (AM) is not used in salt form and/or step b) is not carried out.

The carbonic acid adduct (CAA) preferably remains stable, during storage at a temperature of 2 to 10° C., for at least 12 months, more preferably for at least 13 months, even more preferably for at least 20 months, particularly preferably for at least 23 months, and very particularly preferably for at least 27 months.

The carbonic acid adduct (CAA) is no longer considered stable if the specific bands of the at least one amine (AMO) can be detected by means of IR spectroscopy, in particular in the solid of the carbonic acid adduct (CAA). The specific IR bands of the amine are those bands which are also detected during IR spectroscopic examination of the pure amine (AM). Provided that the amine (AM) is provided in a manner bound in the stable carbonic acid adduct (CAA), the specific IR bands of the amine (AM) are not detected.

In some embodiments, the loss of stability can also be associated with an increase in the pH, or with measurement of two melting/decomposition ranges, i.e. a range that corresponds to the amine (CAA) and a range that corresponds to the carbonic acid adduct (CAA). In the case of the carbonic acid adduct that has become unstable by means of at least partial decomposition in the amine (AM) and $CO_2$ and/or water, a change in the dissolution behavior. The carbonic acid adduct CAA) which has become unstable may prove to be of low solubility, or may be incompletely dissolved at least in part.

The carbonic acid adduct (CAA) can be prepared according to a method comprising steps a), optionally b), c), d) and e).

In step a), a solution (A) is provided which comprises at least one solvent, and $CO_2$ dissolved in the at least one solvent.

The solution (A) comprises at least one solvent, and $CO_2$ in dissolved form. Within the context of this invention, $CO_2$ is understood to be carbon dioxide. Within the context of this invention $CO_2$ in dissolved form is understood to be all forms that $CO_2$ assumes upon dissolving. It is thus known, for example for aqueous solutions, that the dissolved $CO_2$ in the solution can be present inter alia in equilibrium as $CO_2$, as carbonic acid, as singly or doubly deprotonated carbonic acid, i.e. as hydrogen carbonate or carbonate.

The solution (A) is obtained in that $CO_2$ is introduced into the at least one solvent. The $CO_2$ can be introduced into the solvent in any forms that are known to a person skilled in the art and are suitable. Preferably gaseous or frozen $CO_2$ in the form of dry ice, more preferably gaseous $CO_2$, is introduced into the solvent. The $CO_2$ can also be introduced under pressure, in particular if gaseous $CO_2$ is introduced into the solution. In this connection, introduction under pressure means that a pressure of above atmospheric pressure, preferably of above 1.01325 bar, is used. For this purpose, the $CO_2$ can be introduced into the solvent in a container, which isolates the solvent from the surroundings such that a pressure can be generated in the container, in particular by means of supplying the $CO_2$, which is above atmospheric pressure, preferably above 1.01325 bar. The $CO_2$ can be introduced into the solution, in particular in gaseous form, in one step or at intervals.

In step a), a person skilled in the can use any suitable solvent. Preferably a polar protic solvent is used as the solvent, and more preferably the solvent is water. Depending on the intended use of the carbonic acid adduct (CAA), the solvent can be used in different degrees of purity. For example, water having the degree of purity "aqua ad iniectabilia" can be used if the carbonic acid adduct (CAA) is intended to be used for pharmaceutical-medical purposes.

Step a) may comprise the substep a1), in which the solvent is preferably cooled to 3 to 8° C., preferably to 5° C., prior to introducing the $CO_2$. The cooling can be carried out by means of all methods that are known to a person skilled in the art and have been identified as being suitable. For example, the cooling can take place by means of storing the solvent in a fridge for a sufficiently long time, until the solvent is at the target temperature. Likewise, external cooling, for example, can be used.

Step a) may comprise the substep a2), in which the $CO_2$ is introduced into the solvent, preferably until a saturation concentration of from 3 to 10 g/l, more preferably until a saturation concentration of from 4.5 to 7.5 g/l is reached, based on the total volume of the solution. The pH of the solution following saturation with $CO_2$ is preferably ≤3.0 to ≤6.0, even more preferably ≤4.3 to ≤4.8. In substep a2), the $CO_2$ is preferably dissolved under pressure, the pressure being 1.5 to 10 bar, more preferably 1.9 to 7 bar, even more preferably 2 to 5 bar.

Step a) may comprise the substep a3), in which the solution (A) preferably obtained in substep a2) is stored at 1 to 10° C., preferably for at least 30 min, more preferably for at least 50 min, even more preferably for at least 60 min; up to at most 5 d (120 h). The solution (A) preferably obtained in substep a2) is preferably stored at 3 to 8° C. for at least 30 min, more preferably for at least 50 min, even more preferably for at least 60 min; up to at most 5 d (120 h).

Step a) preferably comprises all the substeps a1), a2) and a3).

The substeps a1), a2) and a3) are preferably carried out in the sequence whereby a2) follows a1), and a3) follows a2).

Step b) can optionally be carried out, in which the base (BA), which does not correspond to the amine (AM), is dissolved in the solution (A), thereby obtaining the solution (A1), the base (BA) is preferably a hydrogen carbonate or a carbonate, more preferably a hydrogen carbonate, even more preferably sodium hydrogen carbonate.

In step c), the at least one amine (AM) is dissolved in the solution (A) or (A1), thereby obtaining the solution (B).

As defined above, the at least one amine (AM) can be used in step C) both in neutral form and in the form of a salt. The at least one amine (AM) can optionally also be used as a mixture of the neutral form of the amine (AM) and the salt form of the amine (AM). Therefore, the at least one amine (AM) can comprise the neutral amine (AM) and/or the salt form of the at least one amine (AM). The salt form of the at least one amine (AM) is preferably an acid addition salt, and the acid addition salt is preferably a hydrochloride, hydrobromide, hydroiodide, hydrogen sulfate, hydrogen sulfite, hydrogen phosphate, hydromesylate, hydrotosylate, hydroacetate, hydroformiate, hydropropanoate, hydromalonate, hydrosuccinate, hydrofumarate, hydroxalate, hydrotartrate, hydrocitrate, hydromaleate, more preferably a hydrochloride or hydrobromide, even more preferably a hydrochloride of the at least one amine (AM).

The concentration of the amine (AM) in solution (B) is preferably 0.01 to 0.25 g/ml, preferably 0.03 to 0.20 g/ml, more preferably 0.08 to 0.15 g/ml.

Step c) may comprise the substep c2), in which the at least one amine (AM) is dissolved in solution (A) or, when step b) is carried out, in solution (A1), thereby obtaining the solution (B).

In a possible embodiment, when step b) is carried out, the ratio of the amine (AM) to the base (BA) in solution (B) is 2:1 to 5:1, more preferably 3:1 to 4:1, even more preferably 3.23:1 to 3.26:1 [g/g]].

In a further possible embodiment, when step b) is carried out, the molar ratio of the amine (AM) to the base equivalents of the base (BA) in solution (B) is 0.8:1 to 1.5:1, preferably 1.2:1, more preferably 1:1. In this connection, base equivalents means that, when a monovalent base, such as $NaHCO_3$, is used, the molar ratio of the base (BA) to the amine (AM) corresponds to the ratio specified above. When a bivalent base (BA), such as $Na_2CO_3$, is used, based on the molar substance amount of the base (BA) relative to the case when using a monovalent base, only half the base amount is required in order to introduce the same amount of base equivalents. Thus, for example in the case of a ratio of 1:1, when using 10 mmol amine (AM), 10 mmol $NaHCO_3$ is required, but only 5 mmol $Na_2CO_3$.

In a further embodiment, step b) is carried out, and in substep c1) the amine (AM) in the form of the acid addition salt is added, the amine (AM), together with the acid bound thereto, is added in such an amount that the acid bound to the amine (AM) can neutralize the base (BA) to such an extent that the solution (B) assumes a pH of 6 to 8.

Step c) may comprise the substep c2), in which solution (A) is added to solution (B), thereby obtaining the solution (B1).

The concentration of the amine (AM) in solution (B1) is preferably 0.01 to 0.25 g/ml, preferably 0.03 to 0.20 g/ml, more preferably 0.08 to 0.15 g/ml.

Step c) may comprise the substep c3), in which the solution (B) or, if substep c2) is carried out then the solution (B1), is enriched with $CO_2$. The solution (B) is preferably enriched with 2.5 g/l to 9 g/l, more preferably 5 to 7.5 g/l $CO_2$.

Step c) may comprise the substep c4), in which the solution (B) or, if substep c2) is carried out then the solution (B1), is stored at 1 to 10° C., preferably 3 to 8° C., for at least 1 h, preferably 24 h to 120 h, even more preferably 24 to 72 h.

Step c) may comprise the substep c5), in which the solution (B) or, if substep b2) is carried out then the solution (B1), is enriched with $CO_2$ to a total concentration of at least 6 g/l, preferably at least 10 g/l, more preferably at least 12 g/l, even more preferably at 14 g/l, and very particularly preferably at least 15 g/l. Preferably, in substep c5), a further 0.4 to 4.7 g/l, more preferably 1 to 3.5 g/l $CO_2$ are introduced or dissolved, until the required total concentration in solution (B) or (B1) is achieved.

In this case, the term "total concentration" relates to the total concentration of dissolved $CO_2$ in the solution (B) or (B1), including the $CO_2$ which is bound in the carbonic acid adduct (CAA). The total concentration results in an additive manner from the weight increase of the solution due to the added $CO_2$ in all the preceding enrichment steps a2) and/or c3), if carried out, and c5), without taking account of $CO_2$ which is added optionally in the form of hydrogen carbonate or carbonate as the base (BA) of the solution.

The enrichment of the solution (B) or the solution (B1) with $CO_2$ in substep c5), to the required total concentration, can be carried out at a pressure of 2.5 to 10 bar, preferably 4 to 10 bar, more preferably 5 to 10 bar, even more preferably 6 to 10 bar, very particularly preferably 6.5 to 10 bar. During enrichment with $CO_2$ in substep c5), the solution (B) or (B1) is preferably at a temperature of 3 to 8° C., more preferably 5° C.

The enrichment of the solution (B) or (B1) in the substeps c3) and c5) can take place in the same manner as described for step a).

After carrying out step c5), the pH of the solution (B), or, if the substep c2) is carried out then the solution (B1), is preferably ≤7.0.

Step c) preferably comprises all the substeps c1), c2), c3), c4) and c5).

The substeps c1), c2), c3), c4) and c5) are preferably carried out in the sequence whereby c2) follows c1), c3) follows c2), c4) follows c3), and c5) follows c4).

In step d), the solution obtained after completion of step c) is frozen. The solution B) or, after carrying out substep c2) then the solution (B1), is preferably froze in step d).

The solution, preferably solution (B) or B1), that undergoes step d), preferably has a $CO_2$ content of at least 6 g/l, preferably at least 10 g/l, more preferably at least 12 g/l, even more preferably at 14 g/l, and very particularly preferably at least 15 g/l.

The solution obtained after completion of step c), preferably solution (B) or (B1), is preferably frozen at −100° C. to −20° C., more preferably at −90° C. to −30° C., even more preferably at −80 to −40° C., and very particularly preferably at −70 to −50° C.

The freezing of the solution obtained after completion of step c), preferably solution (B) or (B1), can in principle be carried out according to all methods that are known to a person skilled in the art and have been identified as being suitable. For example, the freezing can take place by means of transferring the solution obtained in step c) into a suitable container which is immersed in a coolant. The container is preferably flask-shaped. The container, in which the solution obtained in step c) is located, is preferably immersed in the coolant at an angle of 40°. The coolant can for example consist of a solvent such as methanol, ethanol or acetone which is brought to the desired temperature by means of adding dry ice, or by means of suitable cooling apparatuses such as cryostats.

The freezing preferably takes place at atmospheric pressure, more preferably at 1.01325 bar.

The solution obtained after completion of step c), preferably solution (B) or (B1), is preferably frozen within 0.3 to 60 minutes, more preferably within 1 to 30 minutes, even more preferably within 1.1 to 10 minutes, particularly preferably within 1.5 to 5 minutes.

The solution obtained after completion of step c), preferably solution (B) or (B1), is preferably frozen at a cooling rate of 10 to 100 K/min, more preferably 20 to 80 K/min, even more preferably 30 to 70 K/min, and particularly preferably 40 to 60 K/min.

The container in which the solution obtained after completion of step c), preferably solution (B) or (B1), is located during the freezing process is preferably rotated in the coolant at 10 to 1000 rpm, more preferably 50 to 600 rpm, even more preferably 100 to 400 rpm, and particularly preferably 200 to 300 rpm.

The freezing can take place in accordance with the shell freezing method.

In step e), the solution frozen in step d), preferably solution (B) or (B)1, is stored at −100 to 0° C. for no more than 4 days.

In step e), the solution frozen in step d), preferably solution (B) or (B1), is preferably stored for 1.5 to 4 days, more preferably for 2.5 to 4 days.

In step e), the solution frozen in step d), preferably solution (B) or (B1), is stored at −50° C. to 0° C., more preferably at −30° C. to −5° C., even more preferably at −25 to −10° C., particularly preferably at −20 to −15° C.

The storage can in principle take place, at the defined temperature, in any cooling apparatus known to a person skilled in the art. For example, the storage can be carried out in a freezer or a walk-in freezer.

The method according to which the carbonic acid adduct (CAA) can be prepared can comprise a further step f) which is carried out after step e). In this case, in step f) the solution stored in step e), preferably solution (B) or (B1), is dried, thereby obtaining dried carbonic acid adduct (CAA).

Preferably, in step f), the water is removed from the solution stored in step e), preferably solution (B) or (B1), until a residual content of <0.8 wt. %, more preferably until a residual content of <0.1 wt. % is achieved, based on the total weight of the dried carbonic acid adduct (CAA).

Preferably, in step f), $CO_2$ that is not bound in the carbonic acid adduct (CAA) is removed from the solution stored in step e), preferably solution (B) or (B1), until a residual content of <0.8 wt. %, more preferably until a residual content of <0.1 wt. % is achieved, based on the total weight of the dried carbonic acid adduct (CAA).

The drying can be carried out using all methods that are known to a person skilled in the art and have been identified as being suitable. The drying is preferably carried out by means of freeze-drying, also referred to as lyophilization. In the event of using a freeze-drying method, step d) constitutes the freezing step, and step e) constitutes the ripening step.

The pressure during the drying is preferably 0.01 to 30 mbar, preferably 0.02 to 20 mbar, more preferably 0.03 to 10 mbar, even more preferably 0.03 to 0.5 mbar, and very particularly preferably 0.05 to 0.1 mbar. The pressure is preferably maintained during the entire drying process. During drying, the pressure defined above is preferably reached within 7 h, more preferably within 5 h, and particularly preferably within 4 h of the start of the evacuation process.

A person skilled in the art can determine the end point of the drying from the recordings of the temperature progression. The total drying time in step f) is preferably 10 to 60 h, more preferably 30 to 55 h, particularly preferably 41 to 52 h. The total drying time is defined as the time period between the completion of the storage in step e) and the ending of the drying in step f).

The temperature during the entire drying process in step f) is preferably 0 to 20° C., preferably 4 to 18° C., more preferably 8 to 16° C.

The above-described method for preparing the carbonic acid adduct (CAA), is a further aspect of the invention.

In a further embodiment of the invention, the carbonic acid adduct (CAA) comprises procaine as the amine (AM), carbonic acid, and at least one salt (S), the decomposition point being 65 to 95° C., preferably 70 to 90° C., more preferably 85 to 90° C., or comprising lidocaine as the amine (AM), carbonic acid, and at least one salt (S), the decomposition point being 20 to 45° C., preferably 25 to 45° C., more preferably 30 to 45°, and/or the carbonic acid adduct (CAA) comprising at least one amine (AM), carbonic acid, and optionally at least one salt (S), and remaining stable, during storage at a temperature of 2 to 10° C., for at least 12 months, preferably for at least 13 months, more preferably for at least 20 months, even more preferably for at least 23 months, particularly preferably for at least 27 months.

A further aspect of the invention is a pharmaceutical preparation (PP) comprising the carbonic acid adduct (CAA).

Within the context of this invention, a pharmaceutical preparation (PP) is understood, in principle, to be a composition that comprises the carbonic acid adduct (CAA) and in can in addition comprise further excipients or additives which are suitable for pharmaceutical-medical use.

Furthermore, the pharmaceutical preparation (PP) can comprise further bases that do not correspond to the amine (AM) and may be different from the base (BA). A person skilled in the art can in principle select the additives according to the desired intended use. In this case, said person will take account of the desired form of application.

The pharmaceutical preparation (PP) can in principle be provided in any suitable administration form. It is thus possible for the pharmaceutical preparation (PP) to be present for example in capsule form, as tablets, as a solution, as an ointment, cream, as a gel, as a paste, poultice paste or active ingredient-containing plaster.

The pharmaceutical preparation (PP) can in principle be applied in any suitable application form. A person skilled in the art will select a suitable administration form according to the intended application form. The pharmaceutical preparation (PP) can for example be administered orally, inhalatively, by means of injection, as a plaster, cutaneously comprising at least dermal application, by application to the eyes, by nasal application, by rectal application, and by vaginal application.

When preparing the pharmaceutical preparation (PP), a person skilled in the art can in principle use the methods known in the prior art.

During preparation of the pharmaceutical preparation, the temperature of the mixture of the carbonic acid adduct (CAA) and the excipients, and optionally further bases, used is preferably less than 60° C., preferably less than 50° C., more preferably 0 to 50° C.

During preparation of the pharmaceutical preparation (PP), preferably in the form of an ointment, dispersants, preferably using an ointment preparation means, can be used. In this case, a rotational speed of <2000 rpm is preferably used.

The carbonic acid adduct (CAA) can be rubbed to powder, in isolation or in the presence of further excipients or bases, prior to being processed into the oral administration forms described below, such as tablets, or capsules, or semi-solid administration forms. A person skilled in the part can in principle use the suitable and known technical means for the purpose in question. It is thus possible to use for example mortars or similar suitable devices for grinding steps. A technical aid is preferably used in the rubbing steps, which keeps the mechanical stress of the carbonic acid adduct as low as possible. The grinding is preferably carried out using a mortar.

The powder thus obtained can then for example be pressed into tablets or filled into commercially available capsules, or mixed with suitable excipients and processed into semi-solid administration forms.

One embodiment of the pharmaceutical preparation (PP) relates to a pharmaceutical preparation (PP) that comprises the carbonic acid adduct (CAA) and is applied orally. In this embodiment, the pharmaceutical preparation (PP) is preferably administered in capsules, more preferably in hard gelatin or cellulose capsules, and particularly preferably in hard gelatin capsules. Likewise, in this embodiment the pharmaceutical preparation (PP) can be applied in tablet form.

In this embodiment, the pharmaceutical preparation (PP) preferably comprises at least one excipient (H), preferably selected from starch, in particular maize starch and/or rice starch, dextrane, cellulose ester and $SiO_2$.

Furthermore, in this embodiment the pharmaceutical preparation (PP) can comprise at least one base (BA1) that does not correspond to the amine (AM) and is identical to or different from the base (BA). The base (BA1) is preferably selected from $NaHCO_3$ or $KHCO_3$, more preferably $NaHCO_3$.

The general statements set out above, regarding the pharmaceutical preparation (PP) preferably also apply for this embodiment, in particular also for the preparation of the pharmaceutical preparation (PP) if technically applicable for this embodiment.

In this embodiment, the pharmaceutical preparation (PP) preferably comprises
a) 1 to 99 wt. %, more preferably 15 to 95 wt. %, of the carbonic acid adduct (CAA),
b) 0 to 60 wt. %, more preferably 3 to 50 wt. %, of the base (BA1), and 1 to 90 wt. %, more preferably 2 to 75 wt. %, of the excipient (H), based on the total weight of the pharmaceutical preparation.

The invention furthermore relates to a method for preparing the pharmaceutical preparation (PP) in the embodiment mentioned above for oral application, comprising the steps of:
a) providing a mixture comprising the carbonic acid adduct (CAA) and optionally at least one base (BA1) and/or at least one excipient (H),
b) rubbing the mixture to a powder,
c) processing the powder into an administration form for oral application, optionally
  i) the at least one excipient (H) being selected from starch, in particular maize starch and/or rice starch, dextrane, cellulose ester and $SiO_2$, and/or
  ii) the base (BA1) preferably being selected from $NaHCO_3$ or $KHCO_3$, more preferably $NaHCO_3$, and/or
  iii) the administration form for oral application being a tablet, and/or
  iv) the administration form for oral application being a capsule, preferably a hard gelatin or cellulose capsule, more preferably a hard gelatin capsule, and/or
  v) 1 to 99 wt. %, preferably 15 to 95 wt. %, carbonic acid adduct (CAA) is used, based on the total weight of the pharmaceutical preparation (PP), and/or
  vi) 0 to 60 wt. %, preferably 3 to 50 wt. %, of the base (BA1) is used, based on the total weight of the pharmaceutical preparation (PP), and/or vii) 1 to 90 wt. %, preferably 2 to 75 wt. %, of the excipient (H) is used, based on the total weight of the pharmaceutical preparation (PP).

The invention furthermore relates to a kit for preparing the above-mentioned embodiment of the pharmaceutical preparation (PP) for oral application, comprising:
a) the carbonic acid adduct (CAA),
b) optionally the base (BA1), and
c) the excipient (H).

A further embodiment of the pharmaceutical preparation (PP) relates to a semi-solid pharmaceutical preparation (PP) that comprises the carbonic acid adduct (CAA) and is applied cutaneously. The pharmaceutical preparation (PP) in this embodiment may be applied for example in ointment form, as a cream, as a gel, as a paste, poultice paste or active ingredient-containing plaster.

The general statements set out above, regarding the pharmaceutical preparation (PP) preferably also apply for this embodiment, in particular also for the preparation of the pharmaceutical preparation (PP) if technically applicable for this embodiment.

In this embodiment, the pharmaceutical preparation (PP) preferably comprises at least one excipient (H1) selected from paraffins, in particular viscous and highly fluid paraffins, lanolin, lanolin alcohols, hydrophobic base gel, vegetable oils, animal fats, synthetic glycerides, liquid polyalkylsiloxanes, waxes, Vaseline and starch, in particular maize starch, preferably Vaseline.

Viscous paraffins (*Paraffinum subliquidum*) are understood to mean paraffins that have a viscosity of from 110 to 230 mPas, whereas highly liquid paraffins (*Paraffinum perliquidum*) have a viscosity of from 25 to 80 mPas.

In this embodiment, the pharmaceutical preparation (PP) preferably comprises:
a) 0.1 to 40 wt. %, preferably 0.4 to 10 wt. %, of the carbonic acid adduct (CAA), and
b) 60 to 99.9 wt. %, preferably 80 to 96 wt. % of the excipient (H1), based on the total amount of the pharmaceutical preparation (PP).

The invention furthermore relates to a method for preparing the semi-solid pharmaceutical preparation (PP) according to the embodiment described above, comprising the steps of:
a) rubbing the carbonic acid adduct (CAA) to a powder,
b) mixing the carbonic acid adduct (CAA) powder from step a) with at least one excipient (H1),
optionally
i) the at least one excipient (H1) being selected from paraffins, in particular viscous and highly fluid paraffins, lanolin, lanolin alcohols, hydrophobic base gel, vegetable oils, animal fats, synthetic glycerides, liquid polyalkylsiloxanes, waxes, Vaseline and starch, in particular maize starch, preferably Vaseline, and/or
ii) the temperature in step a) and b) is less than 60° C., preferably less than 50° C., more preferably 20 to 50° C., and/or
iii) when using dispersers and/or ointment preparation means, a rotational speed of <2000 rpm is used, and/or
iv) 0.1 to 40 wt. %, preferably 0.4 to 10 wt. %, of the carbonic acid adduct (CAA), based on the total amount of the pharmaceutical preparation, and/or
v) 60 to 99.9 wt. %, preferably 80 to 96 wt. % of the excipient (H1), based on the total amount of the pharmaceutical preparation (PP) being used.

The invention furthermore relates to a kit for preparing the above-mentioned embodiment, comprising:
a) the carbonic acid adduct (CAA), and
b) the excipient (H1).

A further embodiment of the pharmaceutical preparation (PP) that comprises the carbonic acid adduct (CAA) relates to a pharmaceutical preparation that is applied parenteral, nasally and/or inhalatively.

The general statements set out above, regarding the pharmaceutical preparation (PP) preferably also apply for this embodiment, in particular also for the preparation of the pharmaceutical preparation (PP) if technically applicable for this embodiment.

In this embodiment, the pharmaceutical preparation (PP) is preferably provided as a solution (A2), comprising the carbonic acid adduct (CAA), dissolved $CO_2$, and at least one excipient (H2).

The excipient (H2) is preferably selected from an alkali halide or earth alkali halide, more preferably NaCl and $MgCl_2$, even more preferably NaCl. The excipient (H2) may be identical to the salt (S). Within the context of this invention, amount specifications based on the excipient (H2), provided that this is identical, in individual embodiments, to the salt (S), relate to additional amounts of the excipient (H2) which were not introduced into the pharmaceutical preparation (PP) in the form of a salt (S), as part of the carbonic acid adduct (CAA).

The solution (A2) is preferably obtained by introducing $CO_2$ into a solvent. The solvent is preferably water. The $CO_2$ for preparing the solution (A2) is preferably introduced into the solvent at a temperature of 0 to 8° C., more preferably 0 to 5° C. The $CO_2$ can be introduced into the solvent in the form of a gas, or in solid form, for example as dry ice. The $CO_2$ is preferably introduced into the solvent in the form of a gas. The $CO_2$ can also be introduced into the solution under pressure, until the desired concentration is reached, as described above, for example for sub step a2).

The $CO_2$ for preparing the solution (A2) is preferably introduced into the solvent up to a concentration of at least 3 g/l, more preferably up to 4 g/l, even more preferably 4 g/l to 8 g/l.

In this embodiment, the pharmaceutical preparation (PP), provided that it is obtained by dissolving the carbonic acid adduct (CAA) into the solution (A2), preferably comprises:
a) 0.05 to 100 mg/ml, preferably 0.08 to 50 mg/ml, of the carbonic acid adduct (CAA), and
b) 0 to 20 mg/ml, more preferably 3 to 10 mg/ml of the excipient (H2), based in each case on the total volume of the pharmaceutical preparation (PP).

The invention also relates to a method for preparing the above-described embodiment of the pharmaceutical preparation for parenteral, nasal and/or inhalative application, said method comprising the steps of:
a) providing a solution (A2),
b) dissolving the carbonic acid adduct (CAA) into the solution (A2),
optionally
i) the solution (A2) preferably being obtained by introducing CO2 into a solvent, and/or
ii) the solvent of the solution (A2) being water, and/or
iii) the CO2 for preparing the solution (A2) is introduced into the solvent at a temperature of 0 to 8° C., more preferably 0 to 5° C., and/or
iv) the CO2 being introduced into the solvent of the solution (A2) up to a concentration of at least 3 g/l, preferably at least 4 g/l, even more preferably 4 g/l to 8 g/l, and/or
v) the method comprising the further step c) of dissolving an excipient (H2) into the solution (A2), and/or vi) when carrying out step c), the excipient (H2) is selected from an alkali halide or earth alkali halide, more preferably from NaCl and $MgCl_2$, even more preferably from NaCl, and/or vii) when carrying out step c), 0 to 20 mg/ml, preferably 3 to 10 mg/ml of the excipient (H2), based on the total volume of the pharmaceutical preparation in step c), is dissolved in solution (A2), and/or viii) the temperature of the solution (A2) in step b) and/or step c) being 0 to 8° C., more preferably 0 to 5° C., and/or ix) in step b), 0.05 to 100 mg/ml, preferably 0.08 to 50 mg/ml, of the carbonic acid adduct (CAA) being dissolved into the solution (A2).

A further aspect of the invention is a kit for preparing the above-described pharmaceutical preparation, said kit comprising:

a) the carbonic acid adduct (CAA),
b) the solution (A2), comprising water as the solvent and CO2, preferably in a concentration of at least 3 g/l, preferably at least 4 g/l, even more preferably 4 g/l to 8 g/l, and
c) the excipient (H2), preferably selected from an alkali halide or earth alkali halide, more preferably NaCl and MgCl2, even more preferably NaCl.

The invention furthermore relates to the preparation of the pharmaceutical preparation (PP), in particular also to the embodiments of the pharmaceutical preparation (PP) as described above.

A further aspect of the invention is the use of the carbonic acid adduct (CAA) and the pharmaceutical preparation (PP), as well as the embodiments of the pharmaceutical preparation (PP) individually described above, in a method for anesthesia, for analgesia, for concomitant treatment of cancer, for anti-inflammatory purposes, for promotion of wound healing, in particular in the case of burns, open wounds and scars, for treatment of neurogenic inflammation such as multiple sclerosis, MMN (multifocal motor neuropathy), for treatment of sinusitis, for treatment of asthma, for treatment of rheumatoid arthritis, for treatment of Alzheimer's, for treatment of dementia, for promotion of convalescence and for promotion of anti-aging, for treatment of burn-out syndromes, for treatment of osteoarthritis, for treatment of polyarthritis, for treatment of pain syndrome and general pain, for pre- and post-operative treatment (also in the case of broken bones), for preventative and rehabilitation medicine, for treatment of zoster neuralgia, for treatment of diseases of the abdominal organs, such as the liver, gall bladder, pancreas, intestine, for treatment of gastrointestinal diseases (ulcerative colitis, Crohn's disease), for treatment of Bekhterev's disease, for treatment of chronic pain of the musculoskeletal system, for treatment of diabetes (improvement of the blood sugar levels), for treating edemata, and as comedication for opioids or other analgesics.

The invention will be explained in the following, with reference to examples. Said examples are in each case just one of a plurality of possible embodiments of the invention.

1. Embodiment 1, Preparation of the Carbonic Acid Adduct (CAA)

1.1 Materials

Amine (AM): 68.8 to 110.1 g procaine hydrochloride (e.g. highest-grade, for use as a pharmaceutical active ingredient; Ph.Eur. or of a quality that is suitable for this purpose)

Base (BA): 22.2 to 33.9 g sodium hydrogen carbonate (e.g. highest-grade or of a quality that is suitable for this purpose), Solvent: 630 to 900 ml water (Aqua ad iniectiabilia)

$CO_2$: at least 12.0 g/l carbon dioxide from pressurized gas steel cylinders ($CO_2$ of a suitable quality)

dry ice for preparing freezing mixtures and for cooling methanol, techn. for preparing freezing mixtures 1.2 Step a)

A clean plastics pressure cylinder is filled with water (e.g. Aqua ad iniectiabilia) up to the marking (approx. 800 to 900 ml) and cooled for at least 1 h in the fridge (3 to 8° C.) or by means of external cooling to 5° C.

A carbonic acid solution saturated with carbon dioxide is prepared. For this purpose, $CO_2$ is introduced into the pre-cooled water at intervals and under pressure (1.6 to 8 bar). The hissing (gas escaping via the pressure relief valve) indicates saturation of the solution with $CO_2$. The saturation is controlled by the weight, until 4.0 to 6.0 g $CO_2$ (corresponding to 4.5 to 7.5 g/l) is dissolved. The saturated solution has a pH of ≤4.3 to 4.8. Said carbonic acid-containing water is sealed, and stored in the fridge for at least 1 h.

1.3 Step b)

21.2 g sodium hydrogen carbonate is provided in a second plastics pressure cylinder, mixed with 320 ml cooled $CO_2$-containing water, and dissolved while being swiveled.

1.4 Step c)

The equivalent amount of solid procaine hydrochloride is added to said solution, while the temperature remains the same, a virtually neutral solution being formed which, following addition of a further 320 ml cold carbonic acid-containing water, results in a clear, slightly acidic solution. The solution is enriched with $CO_2$. The solution thus prepared is stored in the fridge for at least 1 h.

Subsequently, the solution is conditioned again using $CO_2$, until a $CO_2$-concentration of 12 g/l is achieved the solution. The pH is checked by means of pH indicator rods. The pH is ≤6.6.

1.5 Step d)

Round-bottomed flasks are pre-cooled. For the purpose of freezing, the reaction solution is measured out into a pre-cooled measuring cylinder, transferred in portions into round-bottomed flasks, and frozen within 1.5-3.5 min per flask (~200 rpm) by means of immersion in a dry ice/methanol freezing mixture (<−60° C.). The immersion angle of the flask on the rotary evaporator is set to approximately 40°.

1.6 Step e)

The flasks comprising the thus frozen goods are sealed using a ground glass joint and stored temporarily in a freezer at −15 to −20° C. for 2 to 4 days.

1.7 Step f)

The flasks that are temperature-controlled in this manner are encased in Styrofoam containers, which are pre-cooled, and said flasks are immediately connected individually to an evacuated (0.060±0.01 mbar, approx. −46° C., tightness test) freeze-drying system, by means of a flexible rubber cone. The valve cocks are carefully opened, and the individual flasks are placed under vacuum. Finally, all the flasks have to be evacuated.

In order to monitor the process, temperature probes are placed at the bottom of the Styrofoam jacket, which probes chart the entire temperature progression during the whole of the drying process. Before the start of the lyophilization, the temperature probes display temperatures of <−5° C.

During the lyophilization, the pressure is 0.07±0.02 mbar. This sublimation pressure is achieved within 4 h and is maintained throughout the entire lyophilization time. The cooling chamber is temperature-controlled to 9 to 15° C. throughout the entire drying process. The end point of the lyophilization is determined graphically from the temperature progression recordings. The total drying time was at most 52 h. The dry lyophilisate is transferred into an amber glass container having a twist-off lid, provided with a desiccant bag, and stored in the fridge at 0 to 15° C.

2. Effect of the $CO_2$ Concentration in the Solution that Undergoes Step d), and the Duration of the Temporary Storage in Step e), on the Storage Stability and the Decomposition Point of the Carbonic Acid Adduct (CAA)

As summarized in table 1, in embodiments 2.2 to 2.8, the total amount of $CO_2$ in the solution that undergoes step d) is varied in each case, and/or the duration of the temporary storage in step e) is varied, compared with embodiment 1.

TABLE 1

Total amount of $CO_2$ in the solution of step d), and storage duration in step e) in embodiments 2 to 8, and the resulting decomposition points and storage stabilities of the respective carbonic acid adducts (CAA)

| Example | Total amount of $CO_2$ in the solution of step d) in g/l | Storage duration in step e), in days | Decomposition point of the carbonic acid adduct (CAA) in ° C. | Storage stability[4] at 3 to 8° C., in months |
|---|---|---|---|---|
| 2.2[2] | approx.[5] 5 | approx. 4 | 71-77 | 3 |
| 2.3[2] | approx. 4 | <1 | 69-76 | 9 |
| 2.4[1] | approx. 6.5 | approx. 3 | 70-82 | 12 |
| 2.5[2] | approx. 7.5 | approx. 5 | 69-81 | 3 |
| 2.6[1] | approx. 15.5 | approx. 4 | 85-90 | >25[3] |
| 2.7[1] | approx. 14.5 | approx. 2.75 | 73-94 | >21[3] |
| 2.8[1] | approx. 14.5 | <1 | 70-80 | 13 |

[1]embodiment;
[2]comparative example, not according to the invention
[3]storage test not yet completed, sample is stable
[4]storage in closed container, repeated opening after heating to room temperature for sampling
[5]within the context of said table 1, the term "appox." denotes a tolerance range of ±5%.

The example pairings 2.2 and 2.6, 2.4 and 2.7, and the examples 2.3 and 2.8 which have approximately the same storage duration in step e), show that doubling or tripling the total amount of $CO_2$ in the solution that undergoes step d) leads to a very significant increase to a disproportional increase in the storage stability. Thus, for example, tripling the total amount of $CO_2$ in the solution that undergoes step d) leads at least to an eight-fold increase in the storage stability in example 2.6 compared with example 2.2 However, it can also be seen from example 2.5, compared with example 2.4, that an increase in the storage duration in step e) beyond 4 days leads to a reduction, again, in the storage stability, despite a higher total amount of $CO_2$.

A sample is no longer considered stable if the specific bands of the free amine (AM), in this case procaine, can be demonstrated by means of IR spectroscopy.

The increased storage stability also correlates with an increase in the decomposition point. If the three abovementioned example pairings are compared with one another, it is clear that the duration of the temporary storage, in combination with the total amount of $CO_2$ in the solution which undergoes step d), has a significant influence on the storage stability. In particular examples 2.6 and 2.7 show a particularly clearly increased storage stability and an increase in the decomposition point.

3. Comparative DSC Tests of Examples 2.8, 2.7 and 2.6

Comparative DSC tests (DSC=Differential Scanning calorimetry) were carried out using the carbonic acid adducts (CAA) of examples 2.8 (sample 1 in FIG. 1), 2.7 (sample 2 in FIG. 1) and 2.6 (sample 3 in FIG. 1).

TABLE 2

Comparative DSC test

| | Sample 1 | Sample 2 | Sample 3 |
|---|---|---|---|
| Peak onset temperature $T_e$ 1st determination [° C.] | 61 | 69 | 75 |
| Peak onset temperature $T_e$ 2nd determination [° C.] | 61 | 69 | 77 |
| Peak offset temperature $T_c$ 1st determination [° C.] | 74 | 80 | 83 |
| Peak offset temperature $T_c$ 2nd determination [° C.] | 74 | 81 | 83 |
| Peak maximum temperature $T_p$ 1st determination [° C.] | 70 | 74 | 79 |
| Peak onset temperature $T_p$ 2nd determination [° C.] | 70 | 74 | 80 |

A displacement of the decomposition point, from sample 1 (example 2.8), via sample 2 (example 2.7), to sample 3 (example 2.6), towards higher temperatures, can be identified from FIG. 1 and table 1. As a result, the decomposition point rises with an increase in the total amount of $CO_2$ in step d), in conjunction with a longer storage duration in step e).

The higher the peak onset temperature and the narrower the peak, the higher the degree of order within the carbonic acid adduct (CAA), and the more stable the product. In this case, the measured data show that the stability of the carbonic acid adduct (CAA) increases from example 2.8, via example 2.7, to example 2.6.

4. Examples for Pharmaceutical Preparations (PP)

4.1 Capsules and Tablets

In the following, the composition of the pharmaceutical preparation (PP) according to the invention, in the embodiment as capsules or tablets for procaine as the amine (AM), will be described by way of example. Commercially available two-piece capsules in the commercially available sizes (5 to 000) can be used for preparing the capsules, which two-piece capsules are filled with the carbonic acid adduct (CAA)-containing powder, comprising procaine as the amine (AM) (rubbing of the active ingredient carbonic acid adduct (CAA), comprising procaine as the amine (AM), optionally together with additives, fillers and glidants) The carbonic acid adduct (CAA) was prepared according to example 1. It has been found that hard gelatin capsules are more suitable, with respect to stability, than cellulose capsules. Thus, by way of example for hard gelatin capsules having 60 and 100 mg active ingredient according to table 3, the filled hard gelatin capsules exhibit no change, even after 12 months of storage in the fridge, and are therefore stable (FIG. 2). The stability is studied by means of IR spectroscopy. Thus, in the case of the hard gelatin capsules, no procaine was detected by IR spectroscopy within the 12 month period, whereas for cellulose capsules a procaine band was measured in the IR spectrum after only a few days. The content is determined at room temperature, by means of UV/VIS spectroscopy. For magistral preparations, according to the European Pharmacopoeia, point 2.9.6, a tolerance range of ±15% is specified, based on the total content including secondary products. The fluctuations in content shown in FIG. 2 are therefore fluctuations that result from the procedure of producing the capsules.

The valid and generally conventional pharmaceutical regulations for preparing (magistral) preparations are applied (for example European Pharmacopoeia, German Pharmaceutics Code).

TABLE 3

Example composition capsules having added $NaHCO_3$ and carbonic acid adduct (CAA) as an active ingredient prepared according to embodiment 1.

| Active ingredient amount [mg] | 30 | 60 | 100 | 120 |
|---|---|---|---|---|
| Additive, e.g. $NaCO_3$ | 21 | 42 | 71 | 84 |
| Filler, e.g. maize starch, incl. $SiO_2$ | 120 | 90 | 120 | 90 |
| Capsule size | 1 | 1 | 0 | 0 |

TABLE 4

Example composition tablets having added $NaHCO_3$ and carbonic acid adduct (CAA) as an active ingredient prepared according to embodiment 1.

| Active ingredient amount [mg] | 30 | 60 | 100 | 120 |
|---|---|---|---|---|
| Additive, e.g. $NaCO_3$ | 21 | 42 | 71 | 84 |
| Filler, e.g. maize starch, incl. $SiO_2$ | 2.5 | 5 | 8.5 | 10 |

4.2 Ointments

In the following, the composition of the pharmaceutical preparation (PP) according to the invention, in the embodiment as ointment, will be described by way of example for procaine as the amine (AM) in the carbonic acid adduct (CAA). When preparing the ointment, the valid and generally conventional pharmaceutical regulations for preparing (magistral) preparations are applied (for example European Pharmacopoeia, German Pharmaceutics Code). When preparing the ointment, high shearing forces are prevented. Furthermore, the temperature during the preparation is also kept locally below 60° C. Thus, the ground carbonic acid adduct (CAA) comprising procaine as the amine (AM), in a mortar which is temperature-controlled by means of a water bath that is temperature-controlled to 40 to 45° C., is introduced into the ointment base, for example Vaseline. Alternatively, it is also possible to use electrical mixing systems, such as are used within the context of conventional pharmacy operation.

TABLE 5

Example composition, ointment and carbonic acid adduct (CAA) as the active ingredient, prepared according to embodiment 1.

| Content [%] | 0.5 | 1.0 | 1.25 | 2 | 4 |
|---|---|---|---|---|---|
| Active ingredient amount [mg] | 25 | 50 | 62.5 | 100 | 200 |
| Ointment base [g] (e.g. Vaseline) | 5 | 5 | 5 | 5 | 5 |

4.3 Diffusibility

In a test using pig intestines, it was possible to demonstrate the diffusibility of the carbonic acid adduct (CAA), comprising procaine as the amine (AM), compared with procaine hydrochloride. The results are summarized in FIG. 3.

The test was carried out in Tyrode's solution, on a pig intestine (fresh from the abattoir). For this purpose, the intestine was rinsed with Tyrode's solution and clamped on a funnel. The inside of the intestine dipped into a container which contained Tyrode's solution together with carbonic acid adduct (CAA) having procaine as the amine, prepared as described in embodiment 1, or procaine hydrochloride (equimolar). Tyrode's solution without any substance was also applied to the outside of the intestine, in order to keep the intestine "fresh" and to supply it with nutrients. The samples were taken from the above solution (outside of the intestine) and studied by means of UV/VIS spectroscopy. The entire test was carried out in a temperature-controlled manner at 35-38° C. in a water bath.

4.4 Parenteral Solutions

In order to prepare a parenteral solution that contains the carbonic acid adduct (CAA) comprising procaine as the amine (AM), the required amount of water (Aqua ad iniectabilia) is cooled to approximately 5±3° C., in a suitable container comprising a stirring bar or the like, and is kept at this temperature. The water is enriched with gaseous carbon dioxide of the required quality, to approx. 3.2 g/l. The corresponding amount of carbonic acid adduct (CAA), comprising procaine as the amine (AM), and sodium chloride, for an isotonic content, is dissolved in this $CO_2$-containing water.

Alternatively, water that is temperature-controlled to approx. 5±3° C. is enriched with $CO_2$, under pressure and in a closed system, such that a significant excess is present (4.5 to 7.5 g/l). The corresponding amounts of carbonic acid adduct (CAA), comprising procaine as the amine (AM), and sodium chloride, are likewise added to this carbonic acid-containing water.

This cold solution that is provided with the carbonic acid adduct (CAA) containing procaine as the amine (AM), and sodium chloride, undergoes sterile filtration under suitable ambient conditions, and corresponding vials are filled therewith. The valid and generally conventional pharmaceutical regulations for preparing (magistral) preparations are applied (for example European Pharmacopoeia).

TABLE 6

Example compositions for parenteral preparations comprising added NaCl, and carbonic acid adduct (CAA) as the active ingredient, prepared according to embodiment 1.

| | Infusion | | | Injection | | |
|---|---|---|---|---|---|---|
| | Content [%] | | | | | |
| | 0.1 | 0.2 | 0.3 | 1 | 2 | 3 |
| Active ingredient amount [mg] | 50 | 100 | 150 | 50 | 100 | 150 |
| Additive (NaCl) [mg] | 440 | 430 | 425 | 37 | 29 | 25 |
| Total volume [ml] | 50 | 50 | 50 | 5 | 5 | 5 |

4.4.1 Stability of Parenteral Solutions

In a real-time test, the stability of a 0.2% infusion solution having an isotonic NaCl content is compared with a 2% injection solution without further additives. As shown in FIG. 4, in each case the tolerance limit of ±15% for the total content is not affected, over the entire period of 12 months. Unlike in the 0.2% infusion solution, in which the decomposition product of the procaine, p-aminobenzoic acid (pABA), cannot be detected over the entire 12 months, for the 2% infusion solution the increasing formation of aminobenzoic acid (pABA) is observed from 6 months, up to 12 months, within the tolerance limit.

In order to determine the corresponding IR data the solutions were frozen and lyophilized, as described in embodiment 1, without further $CO_2$ being added prior to freezing, in order not to falsify the result. The corresponding IR spectra were measured for the solid thus obtained, which spectra did not exhibit any procaine bands during the time period considered. The total content was determined twice in each case, by means of UV/VIS spectroscopy, from the solution and from the lyphilisate.

4.4.2 Influence of the Sodium Chloride and of the $CO_2$ on the Stability of Parenteral Solutions The influence of the sodium chloride and of the dissolved $CO_2$ on the storage stability of injection solutions was studied. For this purpose, 2% injection solutions, as described by way of example in 4.4, were stored at room temperature, with and without addition of sodium chloride, in open and closed containers in each case. Samples were taken at intervals, and the content of p-aminobenzoic acid, a decomposition product of procaine, was determined. As is clear from FIG. 5, the tests clearly show that the isotonic saline solution has a favorable effect on the stability of the solutions. Thus, even after 4 days at room temperature no amount worth mentioning of p-aminobenzoic acid was measured in the samples of the closed vials having an isotonic sodium chloride content. Without the addition of sodium chloride, significant p-amino acid was detected.

In the case of the open samples, this effect was also identified, but after a much shorter time. All the samples in the open containers have significantly decomposed after 4 days. This, together with the findings from the closed vials, indicates that both the additives, $CO_2$ and NaCl (isotonic), have a positive effect on the stability of the injection solutions. The influence of the $CO_2$ is significantly more pronounced than that of the isotonic NaCl content.

The invention claimed is:

1. A method for preparing a carbonic acid adduct (CAA), comprising carbonic acid, at least one amine (AM), and optionally at least one salt (S), the method comprising steps of
   a) providing a solution (A) which comprises at least one solvent, and $CO_2$ dissolved in the at least one solvent,
   optionally b) dissolving a base (BA), which does not correspond to the amine (AM), in the solution (A), thereby obtaining the solution (A1),
   c) dissolving the at least one amine (AM) in the solution (A) or (A1), thereby obtaining the solution (B),
   d) freezing the solution obtained after completion of step c),
   e) maintaining the solution frozen in step d) at −100 to 0° C. for no more than 4 days, wherein the content of $CO_2$ in the solution that undergoes step d) is at least 6 g/l, optionally at least 10 g/l, optionally at least 12 g/l, optionally at least 14 g/l, or optionally at least 15 g/l, optionally the amine (AM) being in the form of a salt.

2. The method of claim 1 wherein step a) comprises at least one of the following substeps:
   a1) cooling the solvent, the solvent optionally being water, to a temperature in the range of 3 to 8° C., or optionally about 5° C.;
   a2) introducing $CO_2$ into the solvent, optionally up to a saturation concentration in the range of: 3 to 10 g/L, or optionally 4.5 to 7.5 g/L, and optionally a pH of the solution following saturation with $CO_2$ is in the range of 3.0 to 6.0, or optionally in the range of greater than 4.3 to 4.8;
   a3) maintaining the solution (A) at 1 to 10° C., or optionally 3 to 8° C., optionally for: at least 30 min, at least 50 min, at least 60 min; and up to 5 days (120 h); the storage optionally takes place at 3 to 8° C.; or
   any combination of substeps a1)-a3), optionally all substeps a1)-a3), and optionally in the sequence whereby a2) follows a1), and a3) follows a2).

3. The method of claim 1, wherein the base (BA) in step b) is a hydrogen carbonate or a carbonate, or optionally a hydrogen carbonate, or optionally sodium hydrogen carbonate.

4. The method of claim 1, wherein step c) comprises at least one of the following substeps:
   c1) dissolving the at least one amine (AM) in the solution (A) or (A1), thereby obtaining the solution (B);

c2) adding solution (A) to solution (B), thereby obtaining the solution (B1);
c3) enriching solution (B) or (B1) with $CO_2$;
c4) storing the solution (B) or (B1) at a temperature in the range of 1 to 10° C., optionally 3 to 8° C., for at least 1 h, optionally 24 h to 120 h, or optionally 24 to 72 h;
c5) enriching the solution (B) or (B1) with $CO_2$ to a total concentration of at least 6 g/L, optionally: at least 10 g/L, at least 12 g/L, at least 14 g/L, or at least 15 g/L;
or any combination of c1) c5);
wherein optionally:
i) the concentration of the amine (AM) in solution (B) or, if substep c2) is carried out then in solution (B1), is in the range of 0.01 to 0.25 g/mL, optionally in the range of: 0.03 to 0.20 g/mL, or 0.08 to 0.15 g/mL;
ii) after carrying out step c5), the pH of the solution (B) or (B1) is less than or equal to 7.0;
iii) when step b) is carried out, the ratio of the amine (AM) to the base (BA) in solution (B) is in the range of 2:1 to 5:1, optionally in the range of: 3:1 to 4:1, or 3.23:1 to 3.26:1 [g/g];
iv) when step b) is carried out, the molar ratio of the amine (AM) to the base equivalents of the base (BA) in solution (B) is in the range of 0.8:1 to 1.5:1, or optionally in the range of 1.2:1, or about 1:1;
v) in step c1), the at least one amine (AM) comprises an acid addition salt, optionally as a hydrohalide, hydrogen sulfate, hydrogen sulfite, hydrogen phosphate, hydromesylate, hydrotosylate, hydroacetate, hydroformiate, hydropropanoate, hydromalonate, hydrosuccinate, hydrofumarate, hydroxalate, hydrotartrate, hydrocitrate, hydromaleate, hydrochloride, or hydrobromide;
or any combination of c1)-c5);
optionally step c) comprises all substeps c1), c2), c3), c4) and c5); optionally wherein substeps c1), c2), c3), c4) and c5) are carried out in the sequence whereby c2) follows c1), c3) follows c2), c4) follows c3), and c5) follows c4).

5. The method of claim 1, where, in step d):
i) the solution (B) or (B1) is frozen at a temperature in the range of: −100° C. to −20° C., optionally −90° C. to −30° C., optionally −80 to −40° C., or optionally −70 to −50° C.;
ii) the solution (B) or (B1) is frozen within 0.3 to 60 minutes, optionally within 1 to 30 minutes, optionally within 1.1 to 10 minutes, or optionally within 1.5 to 5 minutes;
iii) the container in which the solution (B) or (B1) is located during the freezing process is optionally rotated in the coolant at a rate in the range of: 10 to 1000 rpm, optionally 50 to 600 rpm, optionally 100 to 400 rpm, or optionally 200 to 300 rpm;
iv) the solution (B) or (B1) is frozen at a cooling rate in the range of: 10 to 100 K/min, optionally 20 to 80 K/min, optionally 30 to 70 K/min, or optionally 40 to 60 K/min; or
any combination of i)-iv).

6. The method of claim 1, where, in step e):
i) the frozen solution (B) or (B1) is maintained for a period of time in the range of: 1.5 to 4 days, optionally 2.5 to 4 days;
ii) the frozen solution (B) or (B1) is optionally maintained at a temperature in the range of: −50° C. to 0° C., optionally −30° C. to −5° C., optionally −25 to −10° C., or optionally −20 to −15° C.;
or both i) and ii).

7. The method of claim 1 comprising a further step f) which is carried out after step e), of
f) drying the solution stored in step e), thereby obtaining dried carbonic acid adduct (CAA), wherein, in step f), optionally
i) the water is removed from the solution (B) or (B1) until a residual content of less than 0.8 wt. %, optionally less than 0.1 wt. % is achieved, based on the total weight of the drying product (C);
ii) $CO_2$ that is not bound in the carbonic acid adduct (CAA) is removed from the solution (B) or (B1) until a residual content of less than 0.8 wt. %, optionally less than 0.1 wt. % is achieved, based on the total weight of the drying product (C);
iii) the drying is carried out by means of lyophilization;
iv) during the drying, the pressure is in the range of: 0.01 to 30 mbar, optionally 0.02 to 20 mbar, optionally 0.03 to 10 mbar, optionally 0.03 to 0.5 mbar, optionally 0.05 to 0.1 mbar, said pressure optionally maintained throughout the entire drying process;
v) the pressure during the drying according to iv) is reached within 10 h, optionally within 7 h, optionally within 5 h, and optionally within 4 h of the start of the evacuation process, and/or
vi) the temperature during the entire drying process in step f) is in the range of: 0 to 20° C., optionally 4 to 18° C., or optionally 8 to 16° C.;
vii) the total drying time is in the range of: 10 to 60 h, optionally 30 to 55 h, or optionally 41 to 52 h; or
any combination of i)-vii).

8. The method of claim 1 comprising, wherein at least one amine (AM) according to one of the following formulae (I) or (II) is used,

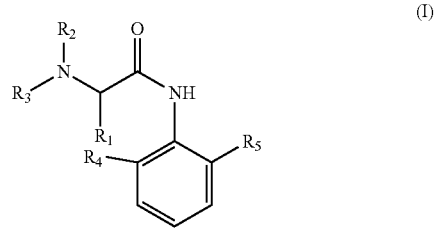

(I)

wherein, in formula (I) $R_1$ is H, $C_{1-10}$ alkyl, $C_{2-10}$ alkenyl, aryl or heteroaryl, optionally H or $C_{1-10}$ alkyl, optionally H or $C_{1-4}$ alkyl; $R_2$ is H, $C_{1-10}$ alkyl, $C_{2-10}$ alkenyl, aryl or heteroaryl, optionally H or $C_{1-10}$ alkyl, optionally H or $C_{1-4}$ alkyl; $R_3$ is H, $C_{1-10}$ alkyl, $C_{2-10}$ alkenyl, aryl or heteroaryl, optionally H or $C_{1-10}$ alkyl, optionally H or $C_{1-4}$ alkyl; wherein it is optionally possible for $R_1$ and $R_3$ to be linked together and to form a saturated or unsaturated, optionally a saturated ring, together with the nitrogen atom to which R3 is bound and the carbon atom to which $R_1$ is bound, and the ring is optionally 4-, 5- or 6-membered, optionally 5- or 6-membered; $R_4$ is H, halogen, $C_{1-10}$ alkyl, $C_{2-10}$ alkenyl, aryl or heteroaryl, optionally H or methyl; $R_5$ is H, halogen, $C_{1-10}$ alkyl, $C_{2-10}$ alkenyl, aryl or heteroaryl, optionally H, methyl or halogen;

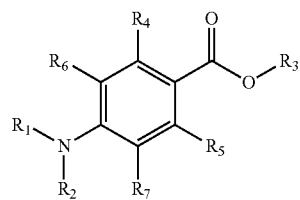

(II)

wherein, in formula (II)

$R_1$ is H, $C_{1-10}$ alkyl, $C_{2-10}$ alkenyl, aryl or heteroaryl, optionally H or $C_{1-10}$ alkyl, optionally H; $R_2$ is H, $C_{1-10}$ alkyl, $C_{2-10}$ alkenyl, aryl or heteroaryl, optionally H or $C_{1-10}$ alkyl, optionally H; $R_3$ is H, $C_{1-10}$ alkyl, $C_{2-10}$ alkenyl, aryl, heteroaryl or —($CH_2$)$_n NR_8 R_9$, optionally —($CH_2$)$_n NR_8 R_9$, n is 1 to 5, optionally 1 to 3, optionally 1 to 2, $R_8$ is C1-10 alkyl, optionally $C_{1-2}$ alkyl, $R_9$ is $C_{1-10}$ alkyl, optionally $C_{1-2}$ alkyl; $R_4$ is H, halogen, $C_{1-10}$ alkyl, $C_{2-10}$ alkenyl, aryl, heteroaryl or alkyl, optionally H, halogen, $C_{1-10}$ alkyl or —O—$C_{1-10}$ alkyl, optionally H or halogen; $R_5$ is H, halogen, $C_{1-10}$ alkyl, $C_{2-10}$ alkenyl, aryl, heteroaryl or —O—$C_{1-10}$ alkyl, optionally H, halogen, $C_{1-10}$ alkyl or —O—$C_{1-10}$ alkyl, more optionally H or halogen; $R_6$ is H, halogen, $C_{1-10}$ alkyl, $C_{2-10}$ alkenyl, aryl, heteroaryl or —O—$C_{1-10}$ alkyl, optionally H, halogen, $C_{1-10}$ alkyl or —O—$C_{1-10}$ alkyl, optionally H or alkyl; $R_7$ is H, halogen, $C_{1-10}$ alkyl, $C_{2-10}$ alkenyl, aryl, heteroaryl or —O—$C_{1-10}$ alkyl, optionally H, halogen, $C_{1-10}$ alkyl or —O—$C_{1-10}$ alkyl, optionally H or —O—$C_{1-10}$ alkyl; wherein the at least one amine according to formula (I) and (II) can optionally also be used in the form of a salt.

9. The method of claim 1, wherein at least one amine (AM) is used that is selected from the group consisting of 4-aminobenzoic acid-2-(N,N-diethylamino-)ethylester (procaine), 4-aminobenzoic acid ethyl ester (benzocaine), 2-(diethylamino)ethyl-4-amino-2-chlorobenzoate (chloroprocaine), 4-amino-3-butoxybenzoic acid-2-diethylaminoethylester (oxybuprocaine), (2-(dimethylamino)ethyl)-4-(butylamino)benzoate (tetracaine), N-[3-(4-phenoxymethylphenyl)propyl]morpholine (fomocaine), 2-diethylamino-N-(2,6-dimethylphenyl)acetamide (lidocaine), (RS)—N-(2,6-dimethylphenyl)-1-methylpiperidin-2-carboxamide (mepivacaine), (RS)—N-(2-methylphenyl)-2-(propylamino)-propanamide (prilocaine), (RS)-4-methyl-3-[2-(propylamino)-propanamido]thiophene-2-carboxylic acid methyl ester (articaine), (±)-1-Butyl-N-(2,6-dimethylphenyl)-2-piperidincarboxamide (bupivacaine), (S)-1-propyl-2',6'-dimethyl-2-piperidylcarboxyanilide (ropivacaine), 2-(ethylpropylamino)-2',6'-butyroxylidide (etidocaine) and 1-(4-butoxyphenyl)-3-piperidin-1-ylpropan-1-one (dyclonine), optionally 4-aminobenzoic acid-2-(N,N-diethylamino-)ethylester (procaine) and 2-diethylamino-N-(2,6-dimethylphenyl)acetamide (lidocaine), (2-(dimethylamino)ethyl)-4-(butylamino)benzoate (tetracaine), and/or the salts of said compounds.

\* \* \* \* \*